(12) United States Patent
Fisher et al.

(10) Patent No.: US 11,179,044 B2
(45) Date of Patent: *Nov. 23, 2021

(54) METHOD OF MEASURING CARDIAC RELATED PARAMETERS NON-INVASIVELY VIA THE LUNG DURING SPONTANEOUS AND CONTROLLED VENTILATION

(71) Applicant: THORNHILL SCIENTIFIC INC., Toronto (CA)

(72) Inventors: Joseph Fisher, Thornhill (CA); David Preiss, Thornhill (CA); Takafumi Azami, Nagoya (JP); Alex Vesely, Victoria (CA); Eitan Prisman, Toronto (CA); Ron Somogyi, Toronto (CA); Steve Iscoe, Kingston (CA)

(73) Assignee: THORNHILL SCIENTIFIC INC., North York (CA)

( * ) Notice: Subject to any disclaimer, the term of this patent is extended or adjusted under 35 U.S.C. 154(b) by 289 days.

This patent is subject to a terminal disclaimer.

(21) Appl. No.: 15/908,038

(22) Filed: Feb. 28, 2018

(65) Prior Publication Data

US 2018/0344172 A1      Dec. 6, 2018

Related U.S. Application Data

(63) Continuation of application No. 14/925,725, filed on Oct. 28, 2015, now abandoned, which is a
(Continued)

(30) Foreign Application Priority Data

Feb. 19, 2003   (CA) ..................................... 2419622

(51) Int. Cl.
*A61B 5/08*        (2006.01)
*A61B 5/0205*    (2006.01)
(Continued)

(52) U.S. Cl.
CPC ............ *A61B 5/0205* (2013.01); *A61B 5/083* (2013.01); *A61B 5/14551* (2013.01);
(Continued)

(58) Field of Classification Search
CPC . A61B 5/0205; A61B 5/14551; A61B 5/7225; A61B 5/7278; A61B 5/083;
(Continued)

(56) References Cited

U.S. PATENT DOCUMENTS 6,099,481 A     8/2000   Daniels et al.
6,227,196 B1    5/2001   Jaffe et al.
(Continued)

FOREIGN PATENT DOCUMENTS

WO    WO-0174433 A1    10/2001
WO    WO-02072185 A1    9/2002
(Continued)

OTHER PUBLICATIONS

Preiss, David Alan. A new method for measurement of carbon dioxide flux in the lungs during breathing. Diss. 2003 (Year: 2003).*
(Continued)

*Primary Examiner* — Andrey Shostak
(74) *Attorney, Agent, or Firm* — Perry + Currier Inc.

(57) ABSTRACT

A method of identifying alveolar ventilation ($V_A$) in a subject, the method comprising: (1) using a breathing circuit which, at exhalation, keeps exhaled gas separate from inhaled gas and at inhalation, when a first gas set (FGS) flow is less than the subject's minute ventilation ($V_E$), results in a subject inhaling FGS first and then a second gas set (SGS), for the balance of inhalation; (2) setting the FGS flow at a rate greater that $V_E$; (3) measuring an end tidal $CO_2$ concentration at a steady state; (4) progressively lowering the FGS flow until a time equal to a recirculation time of $CO_2$ in the subject; and (5) deriving $V_A$ as the rate of FGS flow
(Continued)

at the intersection between an average PETCO$_2$ in a steady state and a line fit to the PETCO$_2$ values after the rise in PETCO$_2$ values begins until the recirculation time.

1 Claim, 21 Drawing Sheets

Related U.S. Application Data continuation of application No. 13/914,292, filed on Jun. 10, 2013, now abandoned, which is a continuation of application No. 10/545,562, filed as application No. PCT/CA2004/000234 on Feb. 18, 2004, now Pat. No. 8,460,202, and a continuation-in-part of application No. 10/509,068, filed on Mar. 17, 2005, now Pat. No. 7,913,690.

(51) Int. Cl.
*A61B 5/083* (2006.01)
*A61M 16/08* (2006.01)
*A61M 16/20* (2006.01)
*A61B 5/1455* (2006.01)
*A61B 5/00* (2006.01)
*A61M 16/22* (2006.01)

(52) U.S. Cl.
CPC .......... *A61B 5/7225* (2013.01); *A61B 5/7278* (2013.01); *A61M 16/08* (2013.01); *A61M 16/206* (2014.02); *A61M 16/208* (2013.01); *A61M 16/085* (2014.02); *A61M 16/0833* (2014.02); *A61M 16/0858* (2014.02); *A61M 16/202* (2014.02); *A61M 16/205* (2014.02); *A61M 16/22* (2013.01)

(58) Field of Classification Search
CPC .. A61M 16/208; A61M 16/206; A61M 16/08; A61M 16/202; A61M 16/205; A61M 16/0833; A61M 16/085; A61M 16/0858; A61M 16/22
See application file for complete search history.

(56) References Cited

U.S. PATENT DOCUMENTS

| | | | |
|---|---|---|---|
| 6,322,514 B1 | 11/2001 | Holte | |
| 6,439,231 B1 | 8/2002 | Fukunaga et al. | |
| 7,913,690 B2 | 3/2011 | Fisher et al. | |
| 2002/0183643 A1* | 12/2002 | Kuck | A61B 5/0836 600/532 |
| 2002/0185129 A1* | 12/2002 | Fisher | A61B 5/4821 128/203.25 |

FOREIGN PATENT DOCUMENTS

WO WO-03082390 A1 10/2003
WO WO-2004073779 A2 9/2004

OTHER PUBLICATIONS

Preiss, David A., et al. "A Simple Method for Continuous Measurement of VCO 2." Anesthesiology 96.A497 (2002): A497. [Abstract].
Ganz, William, et al. "A new technique for measurement of cardiac output by thermodilution in man." The American journal of cardiology 27.4 (1971): 392-396.0 [Abstract].
Stetz, Christian W., et al. "Reliability of the thermodilution method in the determination of cardiac output in clinical practice." American Review of Respiratory Disease 126.6 (1982): 1001-1004. [Abstract].
Critchley, Lester AH., et al. "A meta-analysis of studies using bias and precision statistics to compare cardiac output measurement techniques." Journal of clinical monitoring and computing 15.2 (1999): 85-91.
Imhoff, Michael, et al. "Noninvasive whole-body electrical bioimpedance cardiac output and invasive thermodilution cardiac output in high-risk surgical patients." Critical care medicine 28.8 (2000): 2812-2818. [Abstract].
Koobi, Tiit, et al. "Comparison of methods for cardiac output measurement." Critical care medicine 29.5 (2001): 1092.
Österlund, Barbra, et al. "A new method of using gas exchange measurements for the noninvasive determination of cardiac output: clinical experiences in adults following cardiac surgery." Acta anaesthesiologica scandinavica 39.6 (1995): 727-732. [Abstract].
Richard, Ruddy, et al. "Non-invasive cardiac output evaluation during a maximal progressive exercise test, using a new impedance cardiograph device." European journal of applied physiology 85.34 (2001): 202-207.
Nottin, S., et al. "Study of the reproducibility of cardiac output measurement during exercise in pre-pubertal children by doppler echocardiography and CO2 inhalation." Archives des maladies du coeur et des vaisseaux 93.11 (2000): 1297-1303. [Abstract].
Sakka, Samir G., et al. "Is the placement of a pulmonary artery catheter still justified solely for the measurement of cardiac output?." Journal of cardiothoracic and vascular anesthesia 14.2 (2000): 119-124. [Abstract].
Zollner, Christian, et al. "Beat-to-beat measurement of cardiac output by intravascular pulse contour analysis: a prospective criterion standard study in patients after cardiac surgery." Journal of cardiothoracic and vascular anesthesia 14.2 (2000): 125-129. [Abstract].
Nakonezny, Paul A., et al. "New ambulatory impedance cardiograph validated against the Minnesota Impedance Cardiograph." Psychophysiology 38.3 (2001): 465-473.
Jin, Xiaohua, et al. "End-tidal carbon dioxide as a noninvasive indicator of cardiac index during circulatory shock." Critical care medicine 28.7 (2000): 2415-2419.
Preiss, David Alan. A new method for measurement of carbon dioxide flux in the lungs during breathing. Diss. Toronto: Graduate Department of Chemical Engineering and applied Chemistry, University of Toronto, 2003.

* cited by examiner

METHOD OF MEASURING CARDIAC RELATED PARAMETERS NON-INVASIVELY VIA THE LUNG DURING SPONTANEOUS AND CONTROLLED VENTILATION

CROSS-REFERENCE TO RELATED APPLICATIONS

This application is a continuation of U.S. application Ser. No. 14/925,725 filed Oct. 28, 2015, which is a continuation of U.S. application Ser. No. 13/914,292 filed Jun. 10, 2013, which is a continuation of U.S. application Ser. No. 10/545,562 filed May 30, 2006, now U.S. Pat. No. 8,460,202, which is a continuation-in-part of U.S. application Ser. No. 10/509,068 filed Mar. 17, 2005, now U.S. Pat. No. 7,913,690, which is a national phase filing, under 35 U.S.C. § 371 of International Application No. PCT/CA2004/000234 filed Feb. 18, 2004, which claims benefit of priority from Canadian Patent Application No. 2,419,622 filed Feb. 19, 2003, the disclosures of which are hereby incorporated by reference in their entirety.

FIELD OF THE INVENTION

This invention discloses a method that calculates non-invasively, via the lung, the total cardiac output, pulmonary blood flow, shunt flow, anatomical and alveolar deadspace, true mixed venous $O_2$ saturation, true mixed venous $PCO_2$, and $PaCO_2$. Furthermore the method can be performed in ventilated subjects, subjects breathing spontaneously, even in the presence of variations in their tidal volume and breathing frequency. Subjects need not perform any respiratory manoeuvre such as hyperventilation or breath holding to perform the test.

BACKGROUND OF THE INVENTION

1. Importance of Cardiac Output

A physician's ability to determine a patient's cardiac output ($\dot{Q}$, the volume of blood pumped by the heart each minute) is important in the assessment of critically ill patients. There are various devices and methods that provide a direct or indirect measure of $\dot{Q}$ (see table 1). The most Common method used in clinical practice is thermo-dilution, established by Ganz et al (1). Commercially manufactured catheters (referred to as Swan-Ganz catheters, named after the inventors) contain multiple lumina, an embedded thermister, and a balloon at the tip. The method requires the insertion of the catheter through the skin to access a large central vein such as the internal jugular, subclavian, cephalic or femoral. When the balloon at the end of the catheter is inflated, the catheter tip is carried along with the flow of blood to the right ventricle of the heart and then into the pulmonary artery. The part of the catheter that remains outside the body has connections that can be attached to electrical sensors that determine the pressure and temperature in the pulmonary artery where the tip of the catheter is positioned. Calculation of $\dot{Q}$ requires the injection of a fixed volume of cool liquid of known temperature into a lumen of the catheter that has its opening part way along its length (usually in a part of the catheter in the right atrium). The thermister at the tip of the catheter will register changes in temperature as the cool liquid, carried by the blood, passes. The extent of dilution of the cold bolus of liquid by warm blood will determine the temporal profile of the temperature change at the tip of the catheter. This is referred to as the thermodilution method of measuring cardiac output (TD$\dot{Q}$).

The popularity of TD$\dot{Q}$ stems from ease of use once the catheter is in place. However, the placing and maintenance of the catheter entails considerable risk and expense. Insertion of the Swan-Ganz catheter is associated with complications that are frequently fatal such as puncture of the carotid or subclavian artery with associated internal haemorrhage or stroke, tension pneumothorax, rupture of the right ventricle, malignant arrhythmias (including fatal ventricular fibrillation), and rupture of the pulmonary artery. As a foreign body violating the skin barrier, a pulmonary artery catheter is a constant threat as a source of blood-born infection that is the greatest risk to heart valves, artificial joints, and other implants. Such infections are medical disasters leading to severe morbidity and death. Furthermore, the use of pulmonary artery catheters to measure TD$\dot{Q}$ is very expensive as it requires admission to an intensive care facility where there is continuous presence of critical care nursing and medical staff. Despite these risks, it is still not the ideal method to measure $\dot{Q}$ as it tends to overestimate $\dot{Q}$ by as much as 10% compared to the Fick method (see below) and, for greatest accuracy, requires repeated measurements as its precision is poor. The variability of repeated single measurements is about 22% and can be reduced to 10% by repeated averages of 3 measurements (2). A single thermodilution measurement is considered to be plus or minus 33% the true value. (3)

Because of the expense and risks of keeping the catheters in place, they are removed as soon as practical, often within 24-48 hours of major heart surgery. Often they are removed while the information they provide can still be clinically useful and well before the patient is no longer at significant risk for relapse. If the patient's health deteriorates, a decision must be made about re-inserting the catheter.

An automated non-invasive method of $\dot{Q}$ monitoring would be very useful in the following clinical scenarios:
 a) Selected low risk patients now routinely undergoing pulmonary artery catheterization for intra- and postoperative monitoring.
 b) Patients whose $\dot{Q}$ would be clinically important to know but in whom the risks and costs of insertion of a pulmonary catheter cannot be justified; this includes ward patients, outpatients or patients in the emergency department or doctor's office.
 c) Patients who are too sick to warrant the added risk of pulmonary artery catheter insertion
 d) High and moderate cardiac risk patients undergoing minor and moderate non-cardiac surgical procedures
 e) Severely ill patients with non-cardiac disease.
 f) Relatively healthy patients undergoing major stressful surgery.
 g) Situations in which $\dot{Q}$ is clinically indicated but there is no access to the expertise and critical care facilities required for the use of the pulmonary artery catheters.
 h) Means of monitoring response to cardiovascular therapy such as for hypertension and heart failure.
 i) As a non-invasive diagnostic test of cardio-pulmonary status.
 j) As a means of assessing cardiovascular fitness.

Despite these many applications, non-invasive methods of $\dot{Q}$ measurements have not obtained widespread clinical acceptance. The most commonly researched methods include ECG bio-impedance (Imhoff, 2000 (4)), and pulsed-wave Doppler esophageal sonography. These methods have good repeatability (5-12) and good limits of agreement with either thermodilution or Fick-based methods but only in some populations of subjects. Each method fails in certain patients groups with such pathologies as very high or low $\dot{Q}$ states as occur in surgical patients, septic shock, exercise or cardiogenic shock.

2. Background Physiology and Definition of Terms

Venous blood returns to the right side of the heart from the muscles and organs with reduced oxygen ($O_2$) and increased carbon dioxide ($CO_2$) levels. Blood from various parts of the body is mixed in the right side of the heart and pumped to the lungs via the pulmonary artery. The blood in the pulmonary artery is known as the mixed venous blood. In the lungs the blood vessels break up into a network of small vessels that surround tiny lung sacs known as alveoli. This network of vessels surrounding the alveoli provides a large surface area for the exchange of gases by diffusion along their partial pressure gradients. After a breath of air is inhaled into the lungs, it dilutes the $CO_2$ left in the alveoli at the end of the previous expiration, thereby establishing a pressure gradient between the partial pressure of $CO_2$ ($PCO_2$) in the mixed venous blood ($P\bar{v}CO_2$) arriving at the alveoli and the alveolar $PCO_2$ ($PACO_2$). The $CO_2$ diffuses into the alveoli from the mixed venous blood diminishing the $PCO_2$ in the blood, and increasing the $PCO_2$ in the alveoli until equilibrium is established between the $PCO_2$ in alveolar capillary blood and the $PCO_2$ in the alveoli. The blood then returns to the left side of the heart via the pulmonary vein and is pumped into the arterial system by the left ventricle. The $PCO_2$ in the arterial blood ($PACO_2$) is now the same as that in the alveoli. When the subject exhales, the gas at the very end of exhalation is considered to have come from the alveoli and thus simultaneously reflects the $PCO_2$ in the pulmonary capillaries and the alveoli; the $PCO_2$ in this gas is called the end-tidal $PCO_2$ ($PETCO_2$).

The volume of gas breathed per minute, or minute ventilation ($\dot{V}E$), is measured at the airway opening (nose and/mouth) and is expressed in L/min. The volume of breathed gas distributed to the alveoli (and thus contributing to gas exchange) is termed the alveolar ventilation ($\dot{V}A$) and is also expressed in L/min. The part of $\dot{V}E$ that does not contribute to gas exchange is termed dead space ventilation. This is divided into the anatomical dead space that consists of the trachea and other gas-conducting tubes leading from the nose and mouth to the alveoli, and the alveolar dead space that is collectively the alveoli that are ventilated but not perfused with blood.

The $\dot{V}E$ during normal breathing provides the $\dot{V}A$ that is required to eliminate the $CO_2$ brought to the lungs. $\dot{V}E$ is controlled by a feedback system to keep $PaCO_2$ at a set level of approximately 40 mmHg. Under steady state conditions, the rate at which $CO_2$ is exhaled from the lungs ($\dot{V}CO_2$) is equal to the rate that it is brought to the lungs, which in turn is equal to the metabolic $CO_2$ production. We define steady state as the condition in which the flux of $CO_2$ at the lungs is equal to the $CO_2$ production and the ($\dot{V}CO_2$, $P\bar{v}CO_2$, and $PaCO_2$ remain steady. If the $\dot{V}CO_2$ is diminished, the $CO_2$ extraction from the mixed venous blood passing by the alveoli will be reduced resulting in an increase in the $PaCO_2$ when that blood reaches the arterial system. As the blood traverses the body, it will pick up additional $CO_2$ and will return to the pulmonary artery with a higher $PCO_2$ than on its previous passage. The time between the change in $\dot{V}CO_2$ and reappearance of the blood with raised $PCO_2$ in the mixed venous circulation is termed the recirculation time which is generally taken as 20-30 s in resting subjects.

3. The Fick Equation

The approach for respiratory-based methods for measuring $\dot{Q}$ non-invasively is described by the Fick equation, a mass balance of any substance across the lungs. The Fick method was originally described for $O_2$ as a method for determining pulmonary blood flow. The Fick relation states that the $O_2$ uptake by the lung is equal to the difference between the pulmonary artery and systemic arterial $O_2$ contents times the $\dot{Q}$. The blood contents originally had to be obtained invasively from blood samples. The same relation holds with respect to $CO_2$. The advantage of using $CO_2$ as the tracer is that mixed venous and arterial blood contents of $CO_2$ may be determined non-invasively. The Fick mass balance equation for $CO_2$ is:

$$\dot{Q} = \frac{\dot{V}CO_2}{C\bar{v}CO_2 - CaCO_2}$$

where $\dot{Q}$ is the cardiac output, $\dot{V}CO_2$ is the rate of elimination of $CO_2$ at the lungs, $C\bar{v}CO_2$ and $CaCO_2$ are the mixed venous and systemic arterial contents of $CO_2$, respectively. $\dot{V}CO_2$ can be measured by a timed collection of expired gas and measuring its volume and $CO_2$ concentration. The term $CaCO_2$ can be calculated using an estimate of arterial $PCO2$ ($PaCO_2$) as derived from the $PCO_2$ of end tidal gas ($PETCO_2$). The hemoglobin concentration (easily obtained from a venous blood sample or a drop of blood from a finger prick) and the relation between blood $PCO_2$ and $CO_2$ content (available from standard physiology texts) are then used to calculate $CaCO_2$.

However, $C\bar{v}CO_2$ is difficult to estimate. The $PCO_2$ of mixed venous blood ($P\bar{v}CO_2$) is difficult to determine as true mixed venous blood is present only in the pulmonary artery, which is inaccessible from the surface. The air in the lungs is in intimate contact with mixed venous blood, but $CO_2$ diffuses rapidly from the mixed venous blood into the alveoli before an equilibrium is established. The $PCO_2$ of the expired gas therefore reflects this equilibrium $PCO_2$ and not the $PCO_2$ of mixed venous blood. The $P\bar{v}CO_2$ can be determined from expired gas only when there has been full equilibration with continuously replenished mixed venous blood or partial equilibration under controlled conditions that allow for back calculation of $P\bar{v}CO_2$ from the $PCO_2$ in expired gas. Hence during rebreathing, the alveolar gas is not refreshed and the mixed venous blood continuously passes the alveoli such that an equilibrium is established whereby the $PETCO_2$ reflects the $PCO_2$ in mixed venous blood.

However, even in this scenario, the $PCO_2$ is not that which exists in the pulmonary artery. Blood in the pulmonary artery has a relatively low $PO_2$. Because of the Haldane effect, the low $PO_2$ allows the $CO_2$ to be carried by the hemoglobin at a relatively low $PCO_2$. When the mixed venous blood is exposed to gas in the alveoli, $O_2$ diffuses into the blood, binds to the hemoglobin and increases the $PCO_2$ needed for a given $CO_2$ content on the hemoglobin (the complimentary aspect of the Haldane effect). All methods based on full or partial equilibration of alveolar gas with $P\bar{v}CO_2$ take into account that the equilibration is to a virtual $PCO_2$ that would exist if the $CO_2$ content of the hemoglobin were the same as in mixed venous blood but the hemoglobin were saturated with $O_2$. We refer to this as the oxygenated mixed venous $PCO_2$ ($P\bar{v}CO2$-oxy). Because the relationship between $PCO_2$ and content of $CO_2$ in blood is known, $C\bar{v}CO_2$ can be calculated from both the true $P\bar{v}CO_2$ (as obtained, for example, from a pulmonary arterial blood sample) and $P\bar{v}CO_2$-oxy (as obtained by some of the non-invasive methods described below)[1].

[1] The $P\bar{v}CO_2$-oxy does not really exist but is a virtual number created by instantaneously oxygenating mixed venous blood before and diffusion of $CO_2$ into the alveoli. The $C\bar{v}CO_2$ is the same in each.

4. Rebreathing—Equilibration Method

One method of measuring $P\bar{v}CO_2$-oxy was introduced by Collier in 1956, and is known as the equilibration method. A bag is pre-filled with a high concentration of $CO_2$ (~10-13%) and the subject exhales and inhales rapidly to and from the bag and $CO_2$ is monitored continuously at the mouth. The object of the test is to find the combination of bag volume and bag concentration of $CO_2$ such that once the gas in the bag mixes with that in the lungs (the concentration of $CO_2$ in the residual gas in the lung at the end of a breath in a healthy person is ~5.5%), the partial pressure of $CO_2$ in the lung is equal to that in mixed venous blood. A flat segment of the $CO_2$ tracing segment indicates that inspired and expired $PCO_2$ are equal. To identify the true $P\bar{v}CO_2$-oxy, the flat segment must occur within the first 3-4 breaths, before recirculation raises the $P\bar{v}CO_2$-oxy (see FIG. 16).

4.1.1 Advantages of the Equilibration Method

The capnograph reading is of gas equilibrated with $P\bar{v}CO_2$-oxy and can be considered a directly measured value as opposed to a value obtained from calculation or extrapolation.

4.1.2 Limitations of the Equilibration Method 4.1.2.1 The $CO_2$ concentration in the bag depends on bag size, the patient's lung volume, and the $P\bar{v}CO_2$-oxy—the last being the unknown value. Therefore, the concentration of $CO_2$ in the bag must be individualized to the patient and thus found by trial and error. The method is therefore difficult to automate fully.

4.1.2.2 In practice, since the characteristic of a suitable endpoint (the plateau of $PCO_2$) is subjective, identification of a suitable plateau is difficult to automate.

4.1.2.3 The manoeuvre of rebreathing from a bag is difficult to perform in mechanically ventilated patients and is therefore not suitable for such patients.

4.1.2.4 Inhaling 10-13% $CO_2$ is very uncomfortable and most people cannot tolerate it. It is particularly uncomfortable to someone who is short of breath or exercising.

4.1.2.5 The method requires an external source of $CO_2$. This makes testing equipment bulky and awkward.

4.1.2.6 The method requires that the subject hyperventilate in order to mix thoroughly the gas in the bag and the lungs before recirculation of blood takes place. This requirement limits the test to those subjects who can perform this manoeuvre and who can provide this degree of cooperation. This excludes patients who have severe lung disease, those who are too young, too confused or too ill to cooperate.

4.1.2.7 The test loads a considerable volume of $CO_2$ into the subject's lungs and at the same time prevents $CO_2$ from leaving the blood for the duration of the test. This has negative consequences for the subject:

4.1.2.7.1 Following the test, the subject must hyperventilate to eliminate the applied $CO_2$ load as well as the volume of metabolically-produced $CO_2$ not eliminated during the test. This may pose a considerable burden for some subjects with lung disease or exercising subjects who are already expending considerable effort to cope with their existing metabolic $CO_2$ load.

4.1.2.7.2 A period of hyperventilation following the test is required to eliminate the $CO_2$. This may be difficult for some subjects to perform and, consequently, they may experience respiratory distress for some time until their $PCO2$ is decreased.

4.1.2.7.3 Repeated tests must be delayed until the extra $CO_2$ is eliminated and the baseline state re-established.

4.1.2.7.4 The test itself may distress the subject and alter the $\dot{Q}$.

5. Rebreathing—Exponential Method

In this technique, a small amount of $CO_2$ is placed in a bag and the subject asked to rebreathe from the bag. The $PETCO_2$s of successive breaths will rise exponentially towards $P\bar{v}CO_2$-ox. A rising exponential curve is then fit to the $PETCO_2$s of these breaths to predict an asymptotic value that is assumed to be the $P\bar{v}CO_2$-oxy (See FIG. 17).

5.1 Advantages of the Exponential Method 5.1.1 There is no requirement for respiratory manoeuvres by the patient.

5.1.2 A smaller $CO_2$ load is placed on the subject in order to perform the test.

5.2 Limitations of the Exponential Method 5.2.1 This is an indirect test in which the $P\bar{v}CO_2$-oxy is not measured directly but calculated from data generated by a test.

5.2.2 As the metabolic production of $CO_2$ is small compared to the size of the lung and bag, the rise of $PCO_2$ occurs over a prolonged period. This severely limits the number of useful data points for accurate extrapolation from an exponential curve, before recirculation.

5.2.3 The most important limitation of this and other methods that use partial equilibration during rebreathing to extrapolate to an asymptote using a single exponential is that the assumptions underlying the method are incorrect. In fact, the method produces two different mathematical profiles: the one describing the washout of $CO_2$ from the lung into the bag is a decreasing exponential whereas the second describing the build-up of $CO_2$ released from the blood into the lung-bag mixture is an increasing exponential (13). Only after the gases in the lung-bag system have become well mixed do the two exponentials resolve to a single exponential. By then, very few breaths (if any) that can provide suitable data for extrapolation from a single exponential can be taken before recirculation.

5.2.4 A continually rising level of CO2 makes this test unpleasant in conscious patients, especially in those exercising or very ill.

5.2.5 The manoeuvre of rebreathing from a bag is difficult to perform in mechanically ventilated patients and is therefore not suitable for such patients.

5.2.6 The method requires an external source of $CO_2$. This makes testing equipment bulky and awkward.

5.2.7 The test loads a volume of $CO_2$ into the subject's lungs and at the same time prevents $CO_2$ from leaving the blood for the duration of the test. Although the extent of the $CO_2$ load on the subject is less than with the equilibration method, the negative consequences for the subject, outlined in the section on the equilibration method discussed above, must be considered.

5.2.8 Priming the rebreathing bag with some $CO_2$ improves the predictive qualities of the asymptote since every data point lies closer to the asymptote, but the increased $CO_2$ concentrations increase the discomfort and the limitations approach those outlined above for the equilibration method.

6.0 Calculating $\dot{Q}$ without First Calculating $P\bar{v}CO_2$-Oxy

Gedeon in 1980 described a method of calculating $\dot{Q}$ in ventilated patients via a differential Fick method that circumvents the need to calculate $P\bar{v}CO_2$-oxy. The underlying assumptions of the method are that $\dot{Q}$ and $P\bar{v}CO_2$ will remain unchanged during a step change in lung $CO_2$ elimination and alveolar $PCO_2$ ($PACO_2$) lasting less than a recirculation time (about 30 seconds). Gedeon proposed reducing lung $CO_2$ elimination by reducing either the tidal volume or respiratory frequency setting of the ventilator. As a modification of this method, Orr et al. proposed leaving the ventilator settings unchanged and reducing lung $CO_2$ elimination by temporarily interposing a dead space between the ventilator and the patient's airway resulting in a transient period of rebreathing previously exhaled gas.

6.1 Theoretical Basis of Gedeon/Orr Method:

The method applies to a subject being ventilated under control conditions in which $CO_2$ elimination and $PETCO_2$ are measured. A test manoeuvre consisting of a transient alteration in the $CO_2$ elimination for a time less than a recirculation time is effected and the resulting "equilibrium" $PETCO_2$ is noted. It is assumed that the $\dot{Q}$ and $P\bar{v}CO_2$-oxy during the test are unchanged from control conditions. The Fick equation for these two conditions can be written as $$\dot{Q} = \frac{\dot{V}CO_2}{C\bar{v}CO_2 - CaCO_2}$$

$$\dot{Q} = \frac{\dot{V}CO_2'}{C\bar{v}CO_2 - CaCO_2'}$$

where $\dot{V}CO_2'$ is the $CO_2$ flux at the lungs during the test and $CaCO_2'$ is the corresponding 'new' arterial content of $CO_2$. These two equations can be combined to yield the differential form of Fick's equation:

$$\dot{Q} = \frac{\Delta \dot{V}CO_2}{\Delta(CaCO)_2}$$

where $\Delta$ denotes a "difference in". Since the $PaCO_2$ and $P\bar{v}CO_2$-oxy lie on the same $CO_2$ dissociation curve, partial pressures of $CO_2$ can be substituted for $CO_2$ content to yield the following relation:

$$\dot{Q} = \frac{\Delta \dot{V}CO_2}{S * \Delta PaCO_2}$$

where S is the slope of the $CO_2$ dissociation curve. Like the conventional non-invasive $CO_2$-based Fick method, the differential Fick method relies on predicting $PaCO_2$ through measurements of $PETCO_2$. However, instead of requiring a calculation of $P\bar{v}CO_2$-oxy, the differential Fick equation assumes no change in $P\bar{v}CO_2$-oxy over the duration of the test, and uses the measured quantities $\dot{V}CO_2$ and $\dot{V}CO_2'$ and well as $PaCO_2$ and $PaCO_2'$ (from $PETCO_2$) to calculate the remaining unknown value in the equation: $\dot{Q}$.

6.2 Advantages of Gedeon/Orr Method 6.2.1 The main advantage is that $P\bar{v}CO_2$ does not need to be calculated.

6.2.2 If the deadspace method is used to alter the $\dot{V}CO_2$, then no change in breathing pattern is required.

6.2.3 The method can, theoretically, be fully automated. (In its present commercial form, the size of the interposed deadspace must still be altered manually).

6.3 Limitations of Gedeon/Orr Method

There are a number of limitations in applying Orr's method to spontaneously ventilating subjects.

6.3.1 In spontaneously breathing subjects, there is considerable breath-to-breath variation in breath size and breathing frequency resulting in a variation in $PETCO_2$. This poses problems with respect to:

6.3.1.1 Identification of $PETCO_2$ and $PETCO_2'$. Long periods of baseline measurements are needed in order to average the end tidal values and identify the $PETCO_2$ to be used as the baseline $PETCO_2$ in the differential Fick equation. The test phase cannot last for more than about 30 seconds (due to recirculation), typically 5 breaths. This leaves little time to determine an accurate average $PETCO_2'$. During prolonged baseline periods of observation, the condition of the patient may change.

6.3.1.2 Calculation of $\dot{V}CO_2$. The variations in $PETCO_2$ are related to variations in $CO_2$ elimination but the relationship is not consistently reflected by the $PETCO_2$. For example, assuming a subject breathing at rest with an average resting breath size, an interposed smaller breath may result in a lower $PETCO_2$ (due to a smaller contribution of alveolar gas to the end tidal sample) but the $CO_2$ elimination from that breath will be diminished. Conversely, a larger breath may result in the same $PETCO_2$ as the resting breath but a greater volume of $CO_2$ is eliminated. The commercial automated Gedeon method (NICO2, Novametrics Medical Systems, Wallingford, Conn., U.S.A.) measures the $CO_2$ eliminated breath-by-breath and therefore must continuously average the values to measure $\dot{V}CO_2$. The NICO2 method of calculating $\dot{V}CO_2$ by real-time integration of continuous measurements of flow (with a pneumotachymeter) and $CO_2$ concentration (with a capnograph) is fraught with potential for errors: a small error in the integration of these two signals with different time delays and time constants results in a much larger error in the calculation of $\dot{V}CO_2$. In addition, the greater the variability of the breath size and $CO_2$ concentrations, the longer the measurement time required for an accurate estimate of $\dot{V}CO_2$.

6.3.2 Calculation of $\dot{V}CO_2'$. Stable transient changes in $\dot{V}CO_2$ cannot be achieved in conscious spontaneously ventilating patients:

6.3.2.1 Interposing a deadspace and raising their $PCO_2$ will stimulate spontaneously breathing conscious subjects to increase their $\dot{V}E$ and $\dot{V}CO_2$ until the $PETCO_2$ is restored.

6.3.2.2 Any change in breath size or frequency during a period of breathing, (a normal occurrence in spontaneously breathing people) changes the $\dot{V}CO_2$ during that period. During inspiration, the deadspace gas is inhaled first followed by fresh gas. A decrease in a breath size or frequency diminishes the volume of fresh gas inhaled (and thus the $\dot{V}CO_2$ for that breath). An increase in breath size or frequency will result in an increased volume of fresh gas delivered to the alveoli.

6.3.2.3 Each breath is an independent event and there is no inherent method to compensate in a subsequent breath for changes in $\dot{V}CO_2$ in the preceding breath. For the method to be implemented, therefore, measures must be taken to ensure that breath size and frequency stay absolutely constant during the test. The NICO2 method has no such built-in aspects. The method can therefore be used only in patients who have precisely uniform breathing pattern such as those that are paralysed and mechanically ventilated.

6.3.3 Identification of $PETCO_2$—$PaCO_2$ gradient. The Gedeon and Orr methods assume, or require the establishment of, a constant gradient between the $PETCO_2$ and the $PaCO_2$. The variation in $PETCO_2$ is due to variations of distribution of fresh gas to various parts of the lung and any one breath does not reflect the overall state of $CO_2$ exchange. On the other hand, such variations are not reflected in the $PaCO_2$ which does reflect the overall exchange of $CO_2$ and remains relatively constant. Therefore, variations in $PETCO_2$ also confound the quantification of the $PETCO_2$—$PaCO_2$ gradient under control conditions. Although Orr provides a number of equations to correct for these limitations, these equations are empirical and do not necessarily apply to a particular patient. For example, they are applied whether or not there is irregular breathing.

The $PETCO_2$—$PaCO_2$ gradient during the test phase when rebreathing occurs is unknown. In the presence of large alveolar deadspace (as commonly occurs in many ill patients) the $PETCO_2$—$PaCO_2$ gradient will change during the rebreathing phase. Orr provides some equations to correct for this but since the volume of the alveolar deadspace is unknown, the applicability of the formula to any particular patient is unknown. This further diminishes the accuracy of calculating $PaCO_2'$.

The manoeuvres required to determine each of the terms required to calculate $\dot{Q}$ ($\dot{V}CO_2$, $\dot{V}CO_2'$, $PETCO_2$, $PETCO_2'$ and $PaCO_2'$) by the Orr/Gedeon/NICO2 method is awkward to implement and prone to errors in measurement in the presence of any variation in breath amplitude or breathing frequency as occurs in spontaneously breathing humans or animals.

6.3.4 The parameter calculated by the differential Fick method as practiced by Gedeon/Orr/Respironics is pulmonary blood flow ($\dot{Q}p$). Pulmonary blood flow may be less than the total cardiac output ($\dot{Q}t$) when, for example, some of the $\dot{Q}$ is shunted from the right side of the circulation (superior vena cava, right atrium, right ventricle, pulmonary artery) into the left side of the circulation without passing through the lungs. This is referred to as "shunt" ($\dot{Q}s$). About 5% of venous blood bypasses the lungs (termed shunted blood) in healthy adults. Much larger shunts occur in many medical conditions such as congenital heart disease, surgical repair of some congenital heart diseases, pneumonia, pulmonary edema, asthma, pulmonary atelectasis, adult respiratory distress syndrome, obesity, pregnancy, liver disease and others. The differential Fick method does not include shunted blood in the calculation of $\dot{Q}$ and other empiric corrections must be made to account for it.

7.0 Kim-Rahn Farhi Method 7.1 Theory:

A unique maneuver was proposed by Rim, Rahn and Farhi, (*J. Appl. Physiol.* 21:1388-44. 1966) as a way to calculate the oxygenated mixed venous $PCO_2$ ($P\overline{v}CO_2$-oxy) as well as the true $P\overline{v}CO_2$ and $PaCO_2$. It is based on a paradigm of taking a breath of $O_2$, holding the breath, and exhaling slowly over a period equal to the recirculation time. Over this time of exhalation, the $CO_2$ from the mixed venous blood will diffuse into the alveoli and $O_2$ will be absorbed. The low $PO_2$ in the red blood cells in the mixed venous blood maximizes the volume of $CO_2$ that can be carried by hemoglobin. Oxygen from the alveoli diffuses into the red blood cells, raising the $PO_2$ and decreasing the affinity of hemoglobin for $CO_2$ (Haldane effect). This releases $CO_2$ from the binding sites on the hemoglobin, making it available for diffusion into the alveoli. With breath holding, $CO_2$ will accumulate in the alveoli and the alveolar $PCO_2$ ($PACO_2$) will rise until it no longer provides a gradient for diffusion from the blood. (This $PCO_2$ is known as the oxygenated mixed venous $PCO_2$ ($P\overline{v}CO_2$-oxy).) However, $O_2$ will continue to diffuse as long as the $PAO_2$ is greater than $P\overline{v}O_2$. Relatively little $CO_2$ need diffuse into the alveoli to reach $P\overline{v}CO_2$-oxy compared to the volume of $O_2$ that is available for uptake before the $PO_2$ in the pulmonary capillary blood is in equilibrium with the $PAO_2$. In other words, the equilibration of $CO_2$ in the alveoli with the mixed venous blood will occur well before that of $O_2$.

Since both $O_2$ and $CO_2$ are contained in the same physical volume, the changes in concentrations of each gas over a short period will reflect the rates of flux of that gas over the same period. Therefore, over a short period, the ratio of $PCO_2$ to $PO_2$ will reflect the respiratory quotient, RQ (defined as the rate of $CO_2$ diffusion from the blood into the alveoli divided by the rate of $O_2$ absorption into the blood from the alveoli). The RQ will initially be highest at the beginning of the breath when the rate of $CO_2$ diffusion into the alveoli is maximal, and will approach 0 when the alveolar $PCO_2$ equals $P\overline{v}CO_2$-oxy. In vitro studies have shown that $PACO_2$ equals the true $P\overline{v}CO_2$ when the RQ=0.32 and equals $PaCO_2$ when RQ is equal to the patient's steady state RQ (typically ~0.8).

7.2 Test Method

The method suggested for performing this test would require a subject to take a maximum breath of 100% $O_2$ and exhale very slowly and maximally. Over the course of this exhalation, expired gas is sampled and analyzed continuously for both $PO_2$ and $PCO_2$. $PO_2$ is graphed vs. $PCO_2$ and the RQ is calculated from the instantaneous slope of tangents to the curves at various $PCO_2$ values as follows:

$$RQ = \frac{slope - (FeO_2 * slope) - FeCO_2}{1 - (FeO_2 * slope) - FeCO_2}$$

These RQ values are then plotted against their respective $PCO_2$ data points resulting in a linear relation as illustrated in FIGS. 4 and 5 of T. S. Kin, H. Rahn, and L. E. Farhi cited above.

7.3 Advantages of the Method 7.3.1 This is the only known non-invasive method by which true $P\overline{v}CO_2$ can be calculated.

7.3.2 The method provides an estimate of $PaCO_2$ not based on assuming a gradient between $PETCO_2$ and $PaCO_2$.

7.3.3 Data generated by the method can be used to calculate the $O_2$ saturation of mixed venous blood.

7.4 Limitations of the Kim-Rahn-Farhi Breath-Hold Method

The main limitation of this method is that it requires the subject to have a large lung capacity, hold his breath, and exhale over a prolonged duration. Patients with conditions such as pulmonary fibrosis, pneumonia, adult respiratory distress syndrome, chronic obstructive lung disease, asthma, obesity, trauma, abdominal and chest surgery, mental obtundation, confusion, pregnancy and many others have marked limitations in their ability to take a large breath. Patients are required to cooperate with their duration of breath holding and rate of exhalation. Many patients who are ill, exercising subjects, children and others are unable to perform this satisfactorily. This method is very awkward to automate or perform on ventilated patients.

8.0 Fisher Method 8.1 Theory

In a steady state, if a subject breathes in a $PCO_2$ equal $P\overline{v}CO_2$-oxy, there will be no gradient for gas exchange and the difference in $PCO_2$ between the inspired $PCO_2$ ($PICO_2$) and the expired $PCO_2$ ($PECO_2$) will be 0. The volume of $CO_2$ diffusing into the alveoli will be maximal when the difference between $PICO_2$ and $PECO_2$ is greatest, i.e., when the $PICO_2$ is 0. Since the change in alveolar $PCO_2$ ($PACO_2$) varies directly as the volume of $CO_2$ diffusing into the alveoli and the volume diffusing into the alveoli varies directly as the gradient, then the difference between the $PICO_2$ and $PECO_2$ will vary inversely as $PICO_2$. In other words, graphing the difference between the $PECO_2$ and $PICO_2$ ($PECO_2$–$PICO_2$) vs. $FICO_2$ will result in a straight line. Since subjects normally breathe room air ($PICO_2$ equals 0 or $O_2$, the control $PETCO_2$ provides the first point on the graph. When subjects inhale gas with any constant value of $PCO_2$, the $PETCO_2$ at the end of an equilibration period not exceeding the time for recirculation will provide a second data point which can be used to define the straight line which crosses the X axis where $PICO_2$ equals $P\overline{v}CO_2$-oxy.

8.2 Test Method:

The subject breathes via a non-rebreathing valve. The inspiratory limb is provided with either fresh gas or test gas with any $PCO_2$. To perform a test, the inspired gas is switched from control gas to test gas for about one recirculation time. The PICO2 of the test gas, the $PETCO_2$ just before the test (when $PICO_2$ was 0), and the $PETCO_2$ of the last breath before recirculation are used to calculate the $P\overline{v}CO_2$-oxy.

8.3 Advantages of the Prior Disclosed Previous Fisher Method:

8.3.1 Any low inspired concentration of $CO_2$ such as 1% is adequate to generate a data point; therefore the subject need not get a large $CO_2$ load.

8.3.2 This Fisher method extrapolates to the $P\overline{v}CO_2$-oxy from a linear function and is therefore easier to calculate and more accurate than with the partial rebreathing test in which data points are fit to an exponential curve for extrapolation to an asymptote.

8.3.3 The $PICO_2$ can be any value, so accurate mixtures of gases are not required.

8.3.4 Assuming arterial $PCO_2$ values ($PaCO_2$) can be obtained from arterial blood sample, for example, the method measures total $\dot{Q}$, not just pulmonary blood flow.

8.3.5 The subject need not carry out any respiratory manoeuvre such as breath holding or hyperventilation.

8.3.6 The method does not entail any rebreathing. Therefore, $O_2$ levels remain stable throughout the test and supplemental $O_2$ is not needed.

8.4 Limitations of the Fisher Method 8.4.1 Uniform breath size cannot be guaranteed in spontaneously breathing subjects. A change of breath size or breathing frequency during the latter parts of the test phase will affect the $PETCO_2$ and thus the calculation of $P\overline{v}CO_2$-oxy. Furthermore, as the subjects are inhaling gas that contains $CO_2$, they may be stimulated to take larger or more frequent breaths.

8.4.2 The test requires an external source of $CO_2$. This must be supplied via a tank of $CO_2$ and a gas blender or via a tank of pre-mixed gas. If more than one test gas is required, then arrangements to blend additional gases must be made or more than one additional gas tank is required. This is inconvenient, costly, and adds complexity to the test method and additional bulk and weight to the test apparatus.

8.4.3 It is very complex to configure an automated system that works for both spontaneously breathing and mechanically ventilated patients.

8.4.4 There is no simple method to adapt currently available ventilators, anaesthetic machines or breathing circuits to provide a known and constant $PICO_2$ for a fixed number of breaths.

8.4.5 The technique is difficult to adapt to anaesthetized patients breathing via a circle circuit in which both the test gas and the anaesthetic gases enter the circuit, especially in the presence of a $CO_2$ absorber removing $CO_2$ from the circuit.

OBJECT OF THE INVENTION

It is therefore a primary object of this invention to provide an improved method and apparatus for the purpose of non-invasively determining cardiac output ($\dot{Q}$) which may be utilized in ventilated subjects, subjects who breath spontaneously or subjects who are under controlled ventilation such as those undergoing surgical procedures under general anesthesia.

It is yet a further object of this invention to provide an improved method and the apparatus related thereto for the purposes of non-invasively determining alveolar ventilation ($\dot{V}A$) and calculating minute $CO_2$ production ($\dot{V}CO_2$), oxygenated mixed venous $PCO_2$ ($P\overline{v}CO_2$-oxy), true mixed venous $PCO_2$ (true $P\overline{v}CO_2$), pulmonary shunt, anatomical dead space, arterial $PCO_2$, at a greater accuracy than prior known non-invasive methods and apparatuses would provide.

It is yet another object of the invention to provide a method of non-invasively calculating the oxygen saturation of mixed venous blood ($S\overline{v}O_2$) which may be utilized to reveal heart failure of septic shock in a patient or the like.

It is yet a further object of this invention to provide an improved method and the apparatus related thereto for the purposes of determining $\dot{Q}$, $\dot{V}_A$, $\dot{V}CO_2$, $P\overline{v}CO_2$-oxy, true $P\overline{v}CO_2$, pulmonary shunt, and anatomical dead space in a non-invasive and fully automated manner.

Further and other objects of the invention will become apparent to those skilled in the art when considering the following summary of the invention and the more detailed description of the preferred embodiments illustrated herein.

SUMMARY OF THE INVENTION

This invention discloses a method and apparatus for calculating all of the $\dot{Q}$ regardless of shunt, calculating the shunt, anatomical and alveolar deadspace, true mixed venous $O_2$ saturation, true mixed venous $PCO_2$, and $PaCO_2$. Furthermore the method and apparatus can be used with ventilated subjects, subjects breathing spontaneously, even with marked variations in their tidal volume and breathing frequency, or subjects undergoing surgery under anaesthesia. Subjects need not perform any respiratory manoeuvre such as hyperventilation or breath holding.

According to one aspect of the invention there is provided an improved method and apparatus for the purposes of determining $\dot{Q}$ and $\dot{V}A$ and calculating $\dot{V}CO_2$, $P\overline{v}CO_2$-oxy, true $P\overline{v}CO_2$, $PaCO_2$, pulmonary shunt, and anatomical dead space which increases the accuracy of these determinations in relation to known methods and apparatus and allows the full automation of the various methods disclosed herein for these determinations and calculations.

The New Method:
1. is insensitive to changes in minute ventilation ($\dot{V}E$), tidal volume and/or respiratory frequency so that the method can be carried out in spontaneously breathing subjects;
2. is simplified and less expensive to construct compared to other non-invasive automated methods of performing the differential Fick technique in that
   a. it does not necessarily require any mechanically activated valves to be actively engaged in the patient circuit
   b. does not require a pneumotachygraph to measure flows
   c. does not require manual adjustment of an interposed dead space (and thus can be totally automated);
   d. The device will be the same for all sizes of adults (one size fits all)
3. is compatible with a number of sequential gas delivery breathing (SGDB) circuits. A SGDB circuit provides for the sequential delivery of two gas sets to the lungs during inhalation. A gas set is composed of one or more gases and vapors. The first gas set (FGS) is provided from the beginning of inhalation and can terminate at some time during inhalation depending on the FGS flow and the $\dot{V}E$, at which time inhalation continues with the delivery of the second gas set (SGS). For the purposes of measuring $\dot{Q}$ and the other physiologic parameters described herein, it is preferred that there is a distinct transition from FGS to SGS and there is no mixing of the gas sets. A small degree of mixing of FGS with SGS during the latter part of inhalation will reduce accuracy of the measured and calculated results. Mathematical corrections can be made to minimize effect of the mixing of FGS with SGS, but cannot completely negate the effects in all circumstances. Therefore, breathing circuits which separate the FGS from the SGS are preferred.
4. the generation and presentation of data will be substantially the same for controlled (mechanical) ventilation and rebreathing so that the algorithms to perform the tests and analyze the data can be substantially the same;
5. can institute an equilibrium steady state within one recirculation time so that the value for $PETCO_2$ will be a true measured value rather than one requiring multiple corrections based on unsubstantiated assumptions;
6. will allow the measurement of a new steady state $PETCO_2$ within one recirculation time and thus actualize the assumption underlying the Differential Fick approach that $P\overline{v}CO_2$ is unchanged;
7. Will minimize the effect of changes in tidal volume on the alveolar ventilation.
8. maintain the alveolar $PO_2$ while making pulmonary blood flow measurements;
9. make all calculations without a requirement to measure breath-by-breath volumes of inspired and expired $CO_2$ or any flows of tidal gases.

According to one aspect of the invention there is provided an improved apparatus and method of identifying the alveolar ventilation ($\dot{V}A$), substantially as illustrated and described herein, preferably the $\dot{V}A$ so determined is utilized to calculate the $\dot{V}CO_2$ as $\dot{V}A \times FETCO_2$, where $FETCO_2$ is the fractional pressure of $CO_2$ in end tidal gas.

In one embodiment of the improved apparatus and method:
a) the Fisher approach is used to determine $P\overline{v}CO_2$-oxy (or)
b) the Kim Rahn Farhi approach is used to determine
   i) $P\overline{v}CO_2$-oxy
   ii) true $P\overline{v}CO_2$
   iii) $PaCO_2$
   iv) true $P\overline{v}CO_2$ plus the information from a pulse oximeter to determine mixed venous hemoglobin $O_2$ saturation (or)
c) the differential $CO_2$ Fick technique of Gedeon and Orr is utilized to determine any combination of
   i) $P\overline{v}CO_2$-oxy
   ii) $\dot{Q}$
   iii) $\dot{V}CO_2$
   iv) $\dot{V}CO_2'$
   v) $PETCO_2$—$PaCO_2$ gradient determined using the $PaCO_2$ as determined by the Kim Rahn Farhi method from data collected while reducing the $\dot{V}CO_2$ in order to perform the Differential Fick method. (or)
d) $\dot{Q}$ is determined via the Kim Rahn Farhi method performed during partial rebreathing using a $CO_2$ Fick method where the
   i) $\dot{V}CO_2$ is calculated with or without the new method as disclosed
   ii) $CaCO_2$ and $C\overline{v}CO_2$ are determined from the $PaCO_2$ and $P\overline{v}CO_2$ respectively derived by the Kim Rahn Farhi method; (or)
e) calculation of the respiratory quotient (RQ) is determined as $PETCO_2/(PIO_2-PEO_2)$; (or)
f) $PaCO_2$ is determined directly via analysis of arterial blood sample, arterialized venous sample, transcutaneous $PCO_2$ electrode, or other methods known to those skilled in the art.

wherein said apparatus or method may be utilized for very accurate non-invasive determination of $\dot{Q}$ and the other indicated parameters.

According to yet another aspect of the invention there is provided an improved method of apparatus for determining $\dot{V}A$, $\dot{V}CO_2$ and calculating $\dot{Q}$, $P\overline{v}CO_2$-oxy, true $P\overline{v}CO_2$, $PaCO_2$, pulmonary shunt, anatomical dead space, and $O_2$ saturation in mixed venous blood; which increases the accuracy of these determinations and calculations in relation to known methods and apparatuses and allows for full automation thereof if necessary by using automated means well known to those skilled in the art, to:
i) induce a step change in $\dot{V}CO_2$ by providing a step change in FGS flow to a SGDB circuit to create, with the control data at rest, two sets of data for said determination utilizing the differential Fick equations; (or)
ii) change the partial pressure of $CO_2$ in FGS of a SGDB circuit to create, with the control data at rest, two sets of data for said determination utilizing the Fisher or the differential Fick equations; (or)
iii) change FGS flow or change the partial pressure of $CO_2$ in FGS in a SGDB circuit to simulate complete or partial breath holding and utilizing the Kim-Rahn-Farhi technique, wherein the $PETCO_2$ of each breath is equivalent to a sequential alveolar sample;

thereby providing more relevant data to calculate desired parameters.

In yet another embodiment of the invention a ventilation circuit and method is provided for using sequential delivery of gas sets in order to identify the minute volume of gas entering the anatomical dead space and the minute volume entering the alveoli and thereby available for gas exchange ($\dot{V}A$). Subsequently, setting FGS flow to substantially equal to or less than $\dot{V}A$ substantially controls $\dot{V}A$. A step reduction in $\dot{V}A$ can then be induced by a step reduction in FGS flow, and resultant effects on end tidal gases such as $CO_2$ can be used in the to calculate $\dot{Q}$ and other parameters as previously set out herein in the Background, disclosures and figures.

In yet another embodiment there is provided a method and apparatus of determining $\dot{Q}$ and the other parameters disclosed by utilizing any SGDB circuit for example, the circuits described and illustrated herein by reducing the FGS flow to said circuit or increasing the $PCO_2$ of FGS to said circuit, independent of the breathing rate thereby allowing for calculations to be made via Differential Fick equations, and/or Fisher method, and/or the Kim-Rahn-Farhi method.

Preferably the method or apparatus previously described wherein the $CO_2$ content as calculated from $P\bar{v}CO_2$-oxy and true $P\bar{v}CO_2$, may be utilized to determine the $O_2$ saturation of mixed venous blood with known relations between $CO_2$ content, $O_2$ saturation and $PCO_2$.

In one embodiment the method or apparatus disclosed may be utilized wherein the arterial $O_2$ hemoglobin saturation, as determined by a non-invasive pulse oximeter, which makes the measurement by shining infrared light through a finger, is utilized with the $O_2$ saturation value in the pulmonary artery as calculated by the Kim Rahn Farhi method, to calculate the fraction of shunted blood (assuming fully oxygenated blood in the end pulmonary capillary) thereof.

Preferably said method or apparatus is utilized to determine the fraction of shunted blood $\dot{Q}s$, which in conjunction with determination of total cardiac output $\dot{Q}T$ (utilizing $PaCO_2$ as determined by the Kim Rahn Farhi method, or available from analysis or arterial blood or determined by transcutaneous $PCO_2$ determination or otherwise known to those skilled in the art, as a term in the Fick equation) and pulmonary blood flow $\dot{Q}_p$ (utilizing $PETCO_2$ in the Fick equation) may be used to determine $\dot{Q}_s$ the pulmonary output via the relationship.

$$\dot{Q}_s = \dot{Q}_t - \dot{Q}_p$$

Preferably the method or apparatus disclosed wherein the $O_2$ saturation of haemoglobin in mixed venous blood ($SaO_2$), as determined therewith, is utilized to reveal a condition in a patient such as septic shock, or heart failure.

DETAILED DESCRIPTION OF THE INVENTION

Detailed Description of the Apparatus

Figure 9:
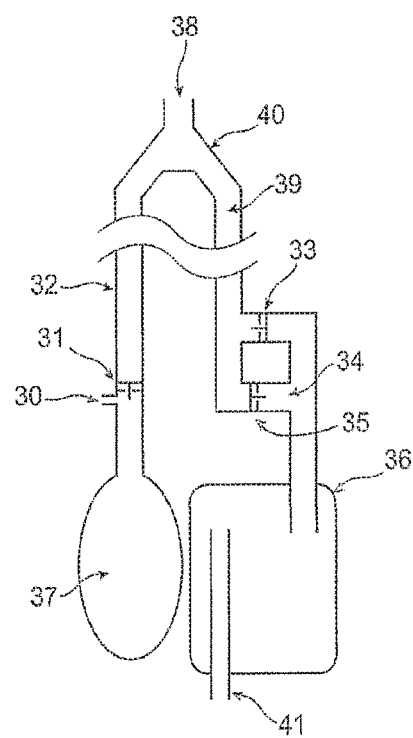
FIG. 9 is a new circuit for use with spontaneous ventilation.
Figure 18:
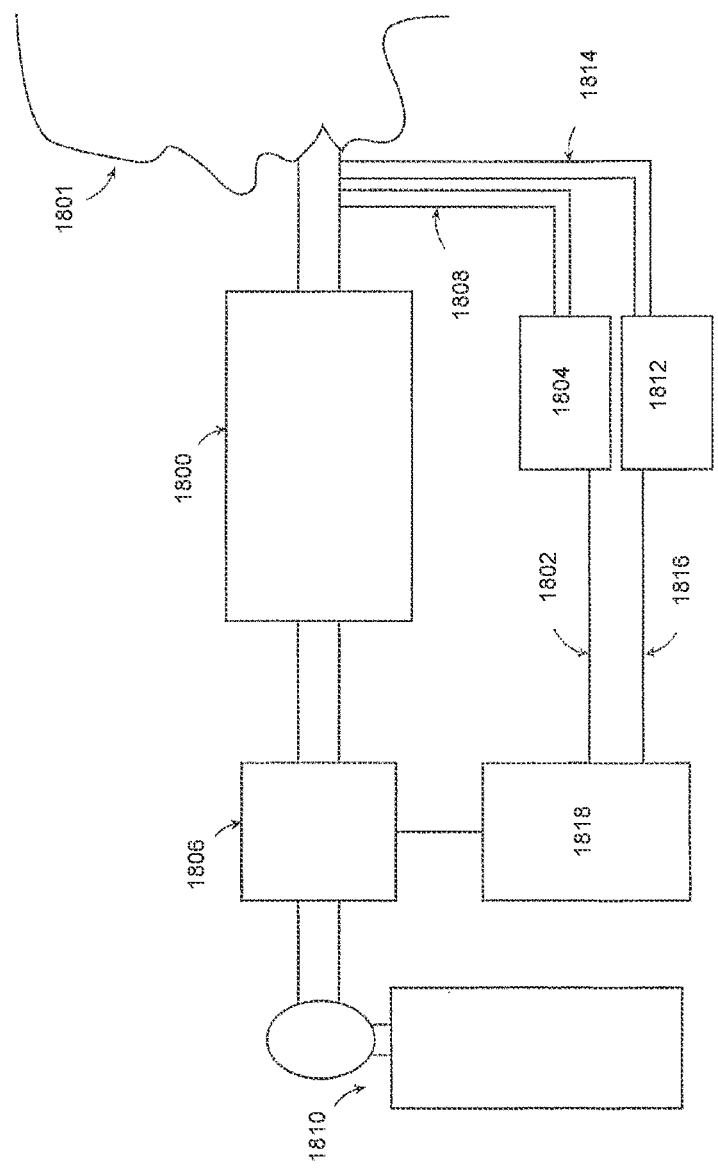
FIG. 18: Apparatus for non-invasive cardiac output apparatus consisting of a breathing circuit, gas sources, gas flow controllers, gas concentration sensors, and microprocessor capable of receiving and storing analog and digital input from sensors and operators, storing and following a decision tree, and generating output signals to a computer screen and to flow controllers.

Referring now to FIG. 18, an apparatus is shown with the following components:

1) a breathing circuit (1800), said breathing circuit preferably has the characteristic that, on exhalation by a subject (1801), exhaled gas is kept separate from inhaled gas and on inhalation, when $\dot{V}E$ is greater than the flow of a first gas set (FGS) into the circuit, the subject inhales FGS gas first and then inhales a second gas set (SGS) gas, preferably said SGS containing CO2 and where SGS may be mostly previously exhaled gas. Any SGDB circuit can be used to greater or lesser benefit, according to its characteristics. We provide below detailed descriptions of several alternate configurations and outline their particular advantages and drawbacks with respect to measuring Q and related parameters outlined above.
2) a gas sample line (1802) leading to a gas analyzer (1804) that monitors the concentration of gases, for example CO2, O2, at the patient-circuit interface 28 and outputs preferably an electric signal corresponding to the concentrations (for example if the gases of interest are O2 and CO2, the "#17500 O2 and $CO_2$ analyzer set" (Vacumed, Ventura Calif., USA))
3) a precise gas flow controller (1806), preferably one that can control the flow of one or more pressurized gases (such as oxygen, air, CO2) singly or in combination, and that can be set manually or via an automated system such as via machine intelligence (for example, the Voltek gas flow controller by Voltek Enterprises, Toronto, Canada);
4) a source of FGS (1810), preferably containing O2 and/or air with or without CO2;
5) means (1812) to identify phase of breathing, for example using electronic pressure sensors with tubing to sample pressures at the patient-circuit interface (1814) or in other locations in the circuit and generating electrical signal corresponding to the sensed pressures. Such means will provide electrical signal (1816). Phase of breathing can also be determined from analysis of gas sensor output by machine intelligence.
6) a computer or machine intelligence (1818) which records, stores, analyzes signals from gas analyzer (204) and pressure transducer (if present), contains a predetermined set of instructions regarding the analysis of data such as calculation of $\dot{Q}$ and physiologic parameters, determination of phase of respiration, display of information on a computer screen, and control of gas flow controller (200) including the timing, sequence and flow of gas.
7) wherein said device may be utilized for non-invasive measurement and determination of $\dot{Q}$ and other parameters such as $\dot{V}A$, $\dot{V}CO_2$, $P\overline{v}CO_2$-oxy, true $P\overline{v}CO_2$, $PaCO_2$, pulmonary shunt, and anatomical dead space Detailed Description of Breathing Circuits FIG. 9 shows a breathing circuit which provides sequential delivery of the FGS followed by the SGS when $\dot{V}E$ exceeds FGSF, with the manifold containing the valves and the FGS reservoir bag and the expiratory gas reservoir bag remote from the patient. This improvement reduces the bulk of the patient manifold, and eliminates the possibility of the SGS mixing with the FGS due to vigorous exhalation.

Referring to FIG. 9, Patient (38) breathes via a Y connector (40). Valve (31) is an inspiratory valve and valve (33) is an expiratory valve. Valve (35) is a bypass valve in the bypass limb (34) that bypasses the expiratory valve (33) and has an opening pressure greater than inspiratory valve (31). Valves (35, 33) may be close to or distal from the patient manifold as desired, as long as they are on the expiratory limb (39). However, in the preferred embodiment, they are distal to the patient to reduce the bulk of the patient manifold. Inspiratory valve (31) may be close to, or distal from, the patient manifold as desired, as long as it is on the inspiratory limb (32). In the preferred embodiment, it is distal to the patient as well. FGS enters the circuit via port (30).

Function:

During exhalation, increased pressure in the circuit closes inspiratory valve (31) and bypass valve (35). Gas is directed into the exhalation limb (39), past one-way valve (33) into the expiratory gas reservoir bag (36). Excess gas is vented via port (41) in expiratory gas reservoir bag (36). FGS enters via port (30) and fills FGS reservoir (37). During inhalation, inhalation valve (31) opens and FGS from the FGS reservoir (37) and FGS port (30) enter the inspiratory limb (32) and are delivered to the patient. If FGSF is less than $\dot{V}E$, the FGS reservoir (37) empties before the end of the breath, and continued respiratory effort results in a further reduction in pressure in the circuit. When the opening pressure of the bypass valve (35) is reached, it opens and gas from the expiratory gas reservoir (36) passes into the expiratory limb (39) and makes up the balance of the breath with SGS.

Thus when FGSF is less than $\dot{V}E$, the subject inhales FGS, then SGS, and no contamination of FGS occurs.

Figure 1:
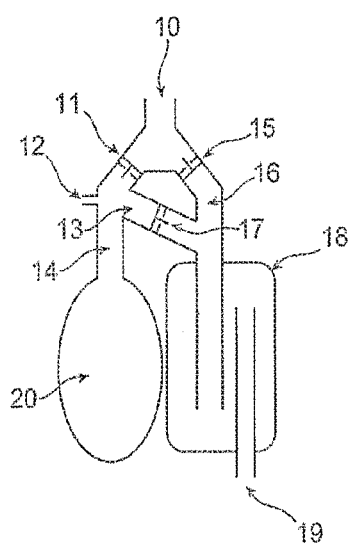
FIG. 1 is a SGDB Circuit as taught by Fisher in U.S. Pat. No. 6,622,725 referred to herein as the Fisher circuit.
Figure 2:
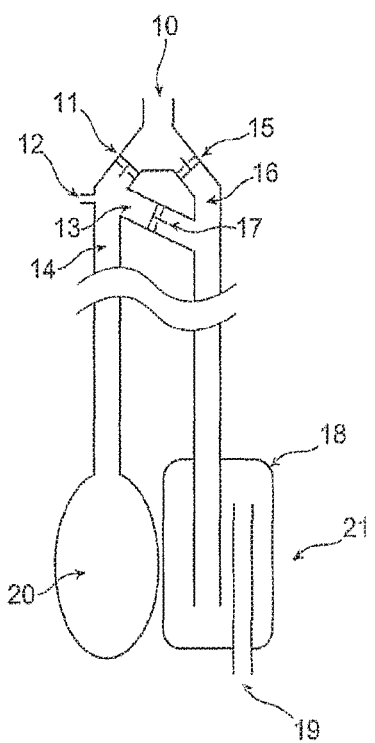
FIG. 2 is similar to FIG. 1 wherein the reservoir bags are remote from the patient.
Figure 3:
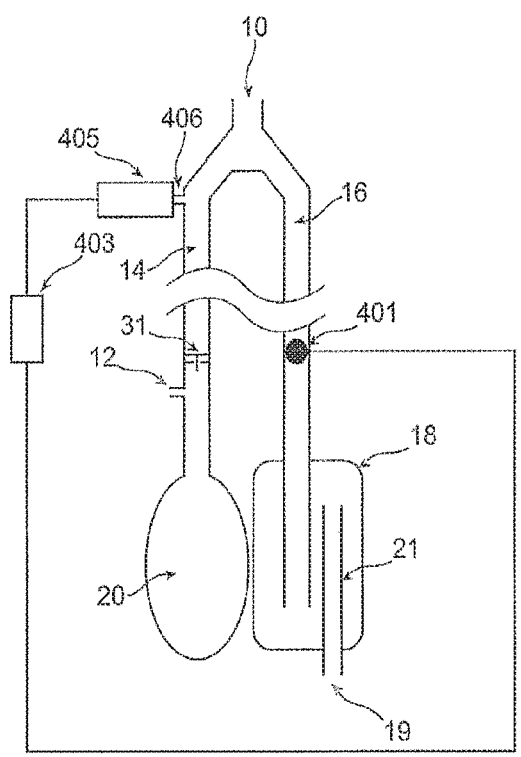
FIG. 3 is similar to FIG. 9 wherein bypass limb, bypass valve, and passive expiratory valve are replaced by an active expiratory valve.
Figure 4:
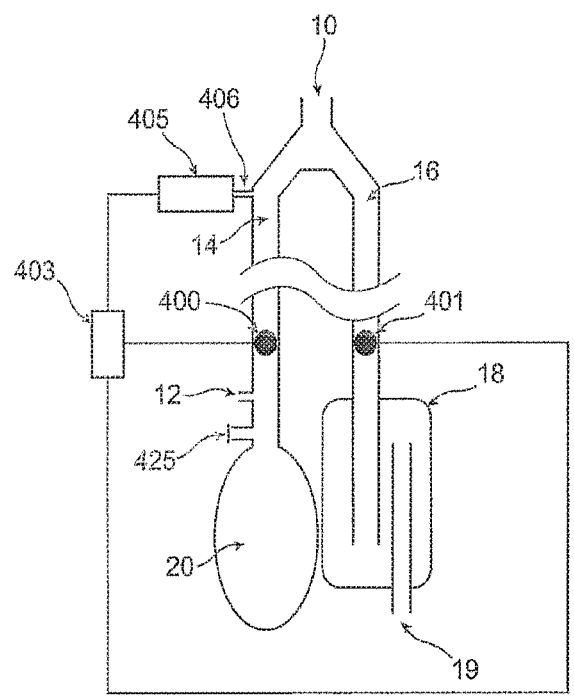
FIG. 4 is similar to FIG. 3 wherein an active valve has replaced the passive inspiratory valve.

FIG. 3 shows an alternate embodiment of the circuit illustrated in FIG. 9 where the passive expiratory valve (33) and expiratory bypass limb (34), and expiratory limb bypass valve (3S) are replaced with a control valve that is triggered by the collapse of the inspiratory reservoir. Referring to FIG. 3, a control valve (401) is placed in the expiratory limb (16) anywhere along its length between the patient port (10) and the expiratory reservoir bag (18). When the patient's VE exceeds the FGSF during inspiration the reservoir bag (20) collapses. This is detected by pressure sensing means (405) through port (406) as an acute reduction in pressure. Pressure sensing means (405) could be an electronic pressure transducer capable of detecting changes 2 cm $H_2O$ pressure, for example. Immediately afterwards, valve (401) is then opened by control means (403), which could be an electronic signal for activating a solenoid valve, for example, leading to depressurization and collapse of a balloon valve, as is known to those skilled in the art, resulting in SGS is being inhaled for the balance of inhalation. During exhalation, patient exhales through expiratory tube (16) past valve (401) into the SGS reservoir (18). At end of exhalation, as detected by pressure sensing means (405) as a reduction of pressure, valve (401) is closed by control means (403), which could be an electronic signal for toggling a solenoid valve, for example, leading to pressurization and inflation of a balloon valve, as is known to those skilled in the art.

While the circuits of FIG. 9 and FIG. 3 present the advantages over the Fisher circuit of reducing the bulk of the patient manifold, and eliminating the possibility of the SGS mixing with the FGS due to vigorous exhalation, they still have the following drawback: When FGS reservoir (20, 37) is emptied and the patient is breathing SGS for the balance of an inspiration, the circuit does not deliver SGS alone but a mixture of SGS and FGS. The FGS continues to flow into the circuit and is drawn by inhalation past one-way inspiratory valve (31, 3) and allows FGS gas to be inhaled from the inspiratory limb (32,14). To optimize the generation of data required to measure of cardiac output, it is necessary to redirect the FGS into the FGS reservoir (37, 20) for the balance of inhalation after the initial collapse of the FGS reservoir. This would prevent mixing of FGS with SGS during the period of inhalation where the patient breathes SGS. This limitation of circuits illustrated in FIGS. 9 and 3 with respect to measuring cardiac output are shared with the Fisher circuit.

Figure 5:
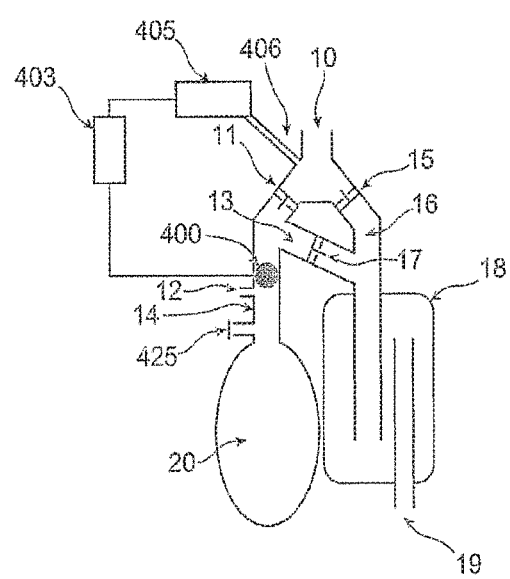
FIG. 5 is similar to FIG. 1 wherein an active valve has been added to the inspiratory limb to prevent mixing of FGS with SGS during inhalation.

FIG. 5 shows an improved circuit that prevents contamination of the SGS by FGS when SGS is being delivered to the patient. Referring to FIG. 5. FGS control valve (400) is added to the inspiratory limb (14) at some point between the FGS port (12) and the inspiratory valve (11). Pop-off valve (425) is connected to the inspiratory limb on the side of the FGS control valve (400) that is proximal to the inspiratory reservoir bag (425). During exhalation, gas passes from the patient port (10), through the expiratory one-way check valve (1S) down the expiratory limb (16) into the expiratory reservoir bag (18). Excess gas exits the expiratory reservoir bag (18) at the opening (19) remote from the entrance. FGS enters the circuit at a constant flow via a fresh gas port (12). As the inspiratory one-way check valve (11) is closed during exhalation, the fresh gas accumulates in the fresh gas reservoir bag (20). During inhalation, FGS entering from the port (12) and the FGS reservoir (20) passes through the inspiratory valve (11) and enters the patient. If the FGSF is less than V̇E, the FGS reservoir bag (20) collapses, as detected by pressure sensing means (405) connected to pressure sensing port (406). FGS control valve (400) is closed via valve control means (403), and valve (17) in the bypass limb (13) opens, directing previously exhaled gas to the patient. When the FGS control valve (400) is closed, any FGSF entering the circuit during the balance of inspiration is directed only to the FGS reservoir bag (20) and not to the patient, who is receiving SGS for the balance of inspiration. FGS control valve (400) may be re-opened any time from the beginning of expiration to just before the next inspiration. FGS control valve (400) may be any type of valve, and is preferably an active valve such as a balloon valve, known to those skilled in the art, that can be controlled by automated means. The pop-off valve (425) opens when the reservoir bag (20) is full to prevent the reservoir bag (20) from overfilling.

Figure 10:
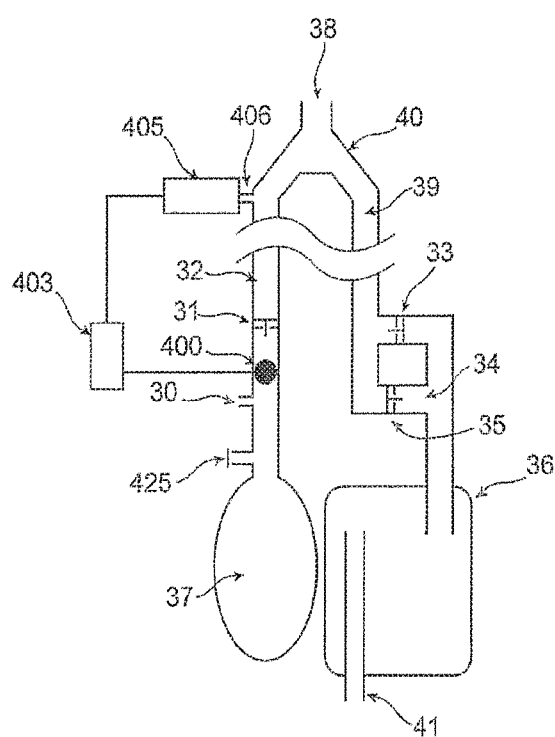
FIG. 10 is similar to FIG. 9 wherein an active valve has been added to the inspiratory limb to prevent mixing of FGS with SGS during inhalation.

The circuit illustrated in FIG. 10 is similar to that in FIG. 9 but has the addition of a FGS control valve (400), together with pressure sensing means (405) and port (406), and valve control means (403), added to the inspiratory limb of the circuit (32) distal to the one-way inspiratory valve (31) and proximal to the FGS inflow port (30). Similarly, a FGS control valve, together with pressure sensing means and port, and valve control means, may be added to the inspiratory limb (14) of the circuit illustrated in FIG. 3 positioned distal to the one-way inspiratory valve (31) and proximal to the FGS inflow port (12) to achieve the same result, namely, prevention of contamination of SGS by FGS when V̇E exceeds FGSF and the FGSF reservoir bag is emptied.

Figure 6:
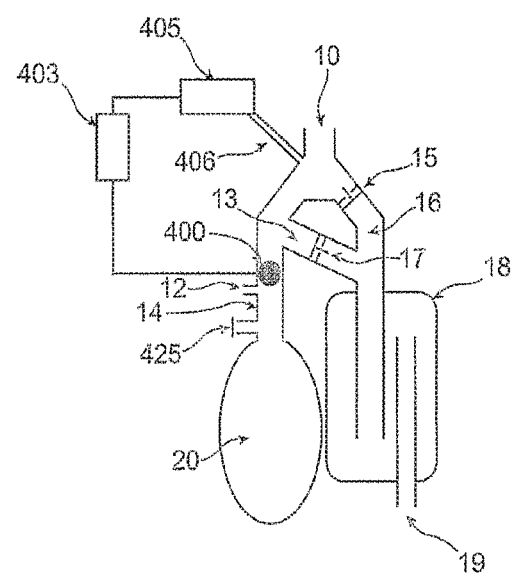
FIG. 6 is similar to FIG. 1 wherein an active valve has replaced the passive inspiratory valve.
Figure 11:
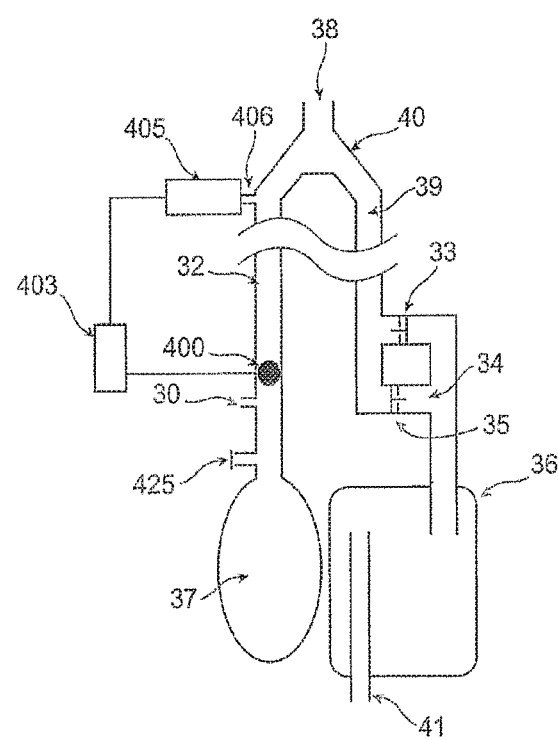
FIG. 11 is similar to FIG. 9 wherein an active valve has replaced the passive inspiratory valve.
Figure 12:
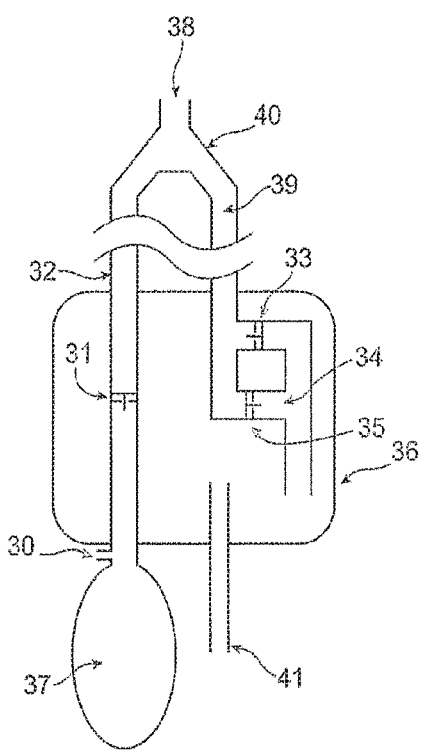
FIG. 12 shows a detail of a circuit design where the passive valves are surrounded by the exhaled gas reservoir

We present two additional circuits that are configured by adding FGS control valve (400) together with pressure sensing means (405) and port (406), and valve control means (403), to the Fisher circuit and the circuit illustrated in FIG. 9 and removing the passive one way inspiratory valve (11, 31), as shown in FIGS. 6 and 11 respectively. These circuits function identically to those illustrated in FIGS. 5 and 10 with respect to complete separation of FGS and SGS during inhalation. In such a circuit, during inspiration, FGS control valve (400) is open until FGSF reservoir bag (20, 37) is emptied, then it is closed so that any additional FGSF entering the circuit during the balance of inspiration is directed only to the reservoir bag (20) and not to the patient. As the patient continues to inspire, bypass valve (17, 35) opens allowing the patient to inhale SGS for the balance of inspiration.

Figure 13:
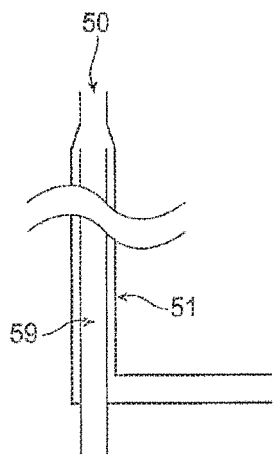
FIG. 13 is a modification of the above circuits to include co-axially arranged inspiratory and expiratory limbs between the valves and the patient.
Figure 14:
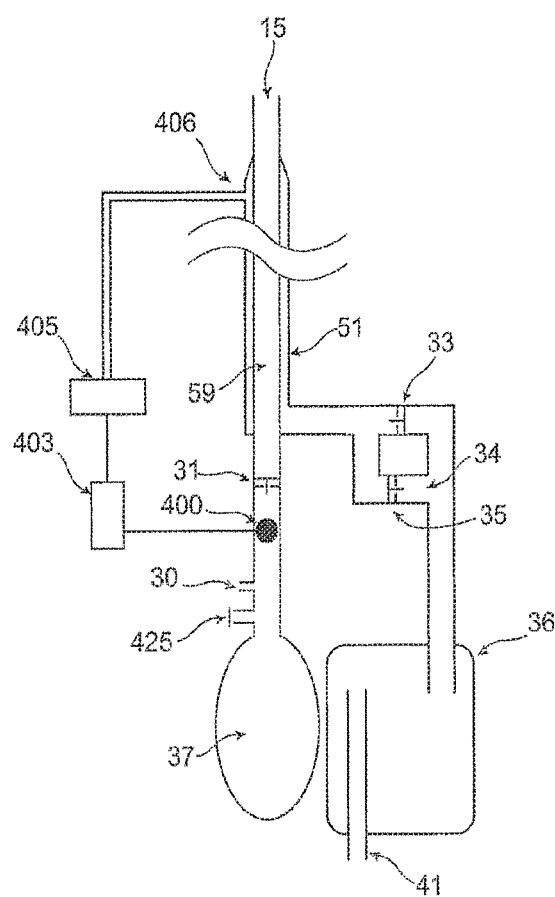
FIG. 14 shows the preferred embodiment of the cardiac output circuit where inspiratory and expiratory limbs are co-axially arranged with the circuit of FIG. 5A.

Another embodiment of each of the circuits whereby the valves can be remote from the patient without loss of sequential delivery of FGS and SGS, such as those illustrated in FIGS. 9, 3, 10, 11, 4, 8, is the replacement of separate inspiratory limbs and expiratory limbs with co-axially arranged inspiratory and expiratory limbs as shown in FIG. 13. FIG. 14 shows the preferred embodiment of the invention: The circuit valves are configured as in the circuit illustrated in FIG. 10 with the improvement of co-axially arranged inspiratory (59) and expiratory (51) limbs. The limbs (51, 59) are co-axial so that one limb is contained within the other for some length of tubing, with the limbs separating at some point along its length, such that the expiratory limb (51) leads to the exhaled gas reservoir (54) and the inspiratory limb (59) leads to the FGS reservoir (56). This has two important advantages over the circuit of FIG. 9:

1. A single tube is connected to the patient interface making it easier to manage sick patients
2. The heat contained in the expiratory limb (51) warms the FGS entering through the inspiratory limb (59).
3. If the inner tube is of a material that allows moisture to pass through it but not gas, such as Nation, will promote moisture exchange as well, so that FGS will become slightly moisturized and more comfortable for the patient to breathe if the SGS is moist. It should be understood that co-axial tubing may be used with any of the SGDB circuits described herein.

DESCRIPTION OF A PREFERRED EMBODIMENT

Referring to FIG. 14, Patient port (50) opens directly to the inspiratory limb (59) and expiratory limb (51) without a Y connector, where the limbs are arranged coaxially. Valve (31) is an inspiratory valve and valve (33) is an expiratory valve. Valve (35) is a bypass valve in the bypass limb (34) that bypasses the expiratory valve (33) and has an opening pressure greater than inspiratory valve (31). Valves (35, 33) are preferably distal from the patient on the expiratory limb (51) to reduce the bulk of the patient interface. Inspiratory valve (31) is also preferably distal from, the patient on the inspiratory limb (59). FGS enters the circuit via port (30). FGS control valve (400) is on the inspiratory limb (59) between port (30) and inspiratory valve (31). FGS reservoir bag (37) is connected to inspiratory limb (59) distal to the patient, past port (37). SGS reservoir bag (36) is distal to the patient on the expiratory limb (51) past expiratory valve (33) and bypass valve (35). Excess expiratory gas vents to the atmosphere via port (41). Pressure sensing means (405) is connected to pressure sensing port (406) which is connected to the patient port (50), and valve control means (403). Pressure sensing port (406) may be connected to the co-axial inspiratory (59) and expiratory limb arrangement (51) anywhere along its length between the inspiratory valve (31) and the patient port (50) or between the expiratory valve (33) and the patient. Pop-off valve (425) is connected to the inspiratory limb on the side of the FGS control valve (400) that is proximal to the inspiratory reservoir bag (425).

Function:

During exhalation, increased pressure in the circuit closes inspiratory valve (31) and bypass valve (35). Gas is directed into the exhalation limb (51), past one-way valve (33) into the expiratory gas reservoir bag (36). Excess gas is vented via port (41) in expiratory gas reservoir bag (36). FGS enters via port (30) and fills FGS reservoir (37). During inhalation, inhalation valve (31) opens and FGS from the FGS reservoir (37) and FGS port (30) enter the inspiratory limb (59) and are delivered to the patient. If FGSF is less than V̇E, the FGS reservoir (37) empties before the end of the breath, and continued respiratory effort results in a further reduction in pressure in the circuit. When the opening pressure of the bypass valve (35) is reached, it opens and gas from the expiratory gas reservoir (36) passes into the expiratory limb (39) and makes up the balance of the breath with SGS. The emptying of FGS reservoir bag (37) is detected by pressure sensing means (405) such as an electronic pressure transducer, known to those skilled in the art, connected to pressure sensing port (406), and FGS control valve (400) such as a balloon valve known to those skilled in the art, is closed via valve control means (403) such as access to gas pressure controlled by an electronically toggled solenoid valve known to those skilled in the art. When the FGS control valve (400) is closed, any additional FGSF entering the circuit during the balance of inspiration is directed only to the FGS reservoir bag (20) and not to the patient, who is inhaling only SGS for the balance of inspiration. FGS control valve (400) may be re-opened any time from the beginning of expiration, as sensed by the reverse of pressure by the pressure sensing means (405), to just before the next inspiration, also sensed by pressure changes in the breathing circuit. Pop-off valve (425) prevents the FGS reservoir bag (20) from overfilling when FGS exceeds V̇E.

Thus when FGSF is less than V̇E, the subject inhales FGS, then SGS, and no contamination of SGS with FGS occurs.

Use of Circuits for Ventilated Patients

Figure 7:
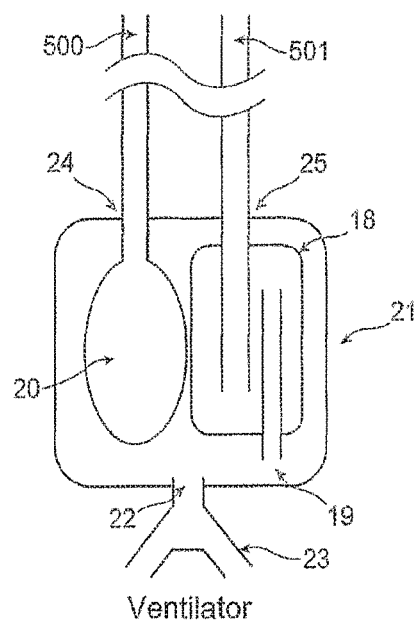
FIG. 7 shows a modification of any of the circuits shown in FIGS. 1, 2-6, 9-11 for use with a mechanically ventilated patient.

Any of the SGDB circuits disclosed herein as well as the Fisher circuit can be used for a patient under controlled ventilation by enclosing the FGS reservoir (20) and exhaled gas reservoir (18) within a rigid container (21) with exit ports for the inspiratory limb of the circuit (24) and expiratory limb of the circuit (25) and port for attachment to a patient interface of a ventilator (22) as illustrated in FIG. 7. In FIG. 7, the inspiratory limb (500) represents the inspiratory limb of any of the SGDB circuits herein described, and expiratory limb (501) corresponds to the expiratory limb of any of the SGDB circuits herein described. The FGS reservoir bag (20) and expiratory gas reservoir bag (18) are enclosed in a rigid air-tight container such that the inspiratory limb (500) enters the container via port (24) and expiratory limb (501) enters the container via port (25) such that the junctions of the outside of the limbs form an air-tight seal with the inside surface of the ports. A further port (22) is provided for attachment of the Y piece of any ventilator (23). Detachment from the ventilator allows the circuit to be used with a spontaneously breathing patient. During the inspiratory phase of the ventilator, the pressure inside the container (21) rises putting the contents of the FGS reservoir bag (20) and the expiratory gas reservoir bag (18) under the same pressure. Since the opening pressure of the inspiratory valve is less than that of the bypass valve for circuits using passive bypass valves (for example those shown in FIGS. 1, 2, 9, 11, 10, 6, and 5, the FGS reservoir (20) will be emptied preferentially. When the FGS reservoir (20) is empty, the pressure in the container (21) and inside the expiratory gas reservoir (18) will open the bypass valve (35, 17, 206) and begin emptying exhaled gas reservoir (18) delivering SGS to the patient. For circuits using an actively engaged control valve (400) in the inspiratory limb of the circuit, a valve opening detection means (407) such as an electronic circuit that is broken by the opening of the valve when the valve is part of a closed electronic circuit, not shown, detects opening of the one way valve (35, 17, 206) in the exhalation bypass limb. The FGS control valve (400) is then closed, directing FGS into the FGS reservoir bag until the collapse of the FGS reservoir during the next inspiratory phase.

During the exhalation phase of the ventilator, the ventilator's expiratory valve is opened and contents of the container (21) are opened to atmospheric pressure, allowing the patient to exhale into the expiratory gas reservoir (18) and the FGS to flow into the FGS reservoir bag (20). Thus, the FGS and SGS are inhaled sequentially during inhalation with controlled ventilation without mixing of FGS with SGS at any time.

Figure 8:
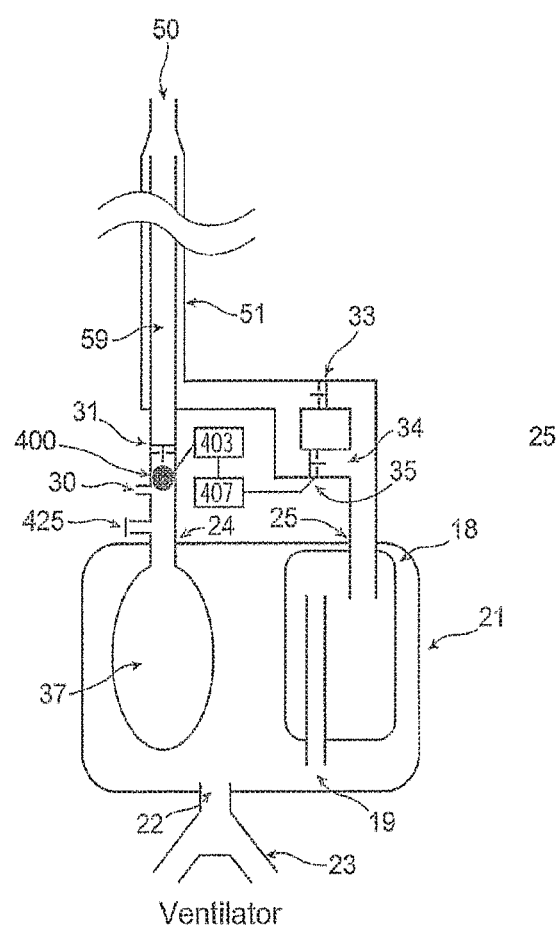
FIG. 8 shows the preferred embodiment modified for use on ventilated patients.

FIG. 8 shows the ventilator configuration described above as used with the preferred circuit shown in FIG. 14. This is the preferred embodiment for ventilated patients.

Figure 20:
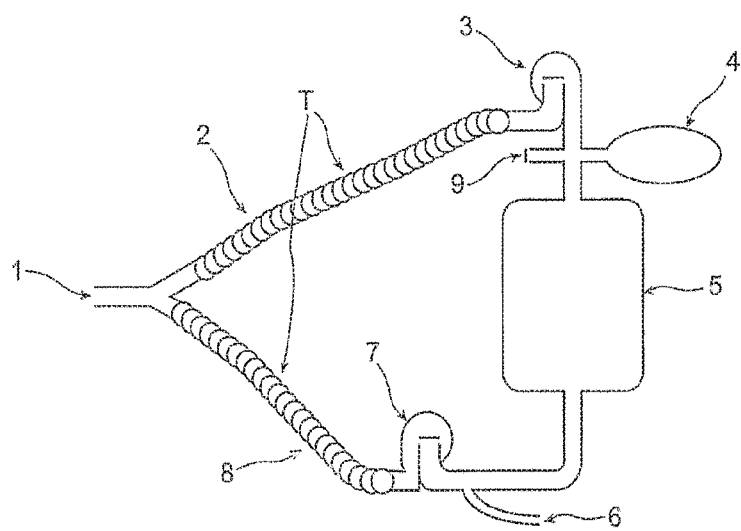
FIG. 20 is a schematic of a standard anesthetic circle system herein provided as reference for discussion of disclosed system. Gas entering the anesthetic circuit consisting of oxygen, with the possible addition of air and/or nitrous oxide ($N_2O$), and possibly an anesthetic vapor such as isoflurane, desflurane or sevoflurane enters the fresh gas port (6) at a constant and known flow. The gas concentrations entering the circuit are set by the anesthesiologist. The patient inspires through the patient port (1) and draws fresh gas plus gas drawn from the gas reservoir bag (4) through the $CO_2$ absorber (5) up the inspiratory limb (8). During exhalation, the inspiratory valve (7) closes and the fresh gas passes through the $CO_2$ absorber (5) towards the gas reservoir bag. Expired gas flows down the expiratory limb (2) displacing gas into the gas reservoir bag (4). When the reservoir bag is full, the pressure in the circuit rises, opening the APL (airway pressure relief) valve (9), and the rest of the expired gas exits the circuit through the APL valve. Gas is sampled continuously at the patient port and is analyzed for concentrations of constituent gases. The inspiratory (2) and expiratory (8) limbs consist of tubing (T).

The primary difference between the standard anesthetic circle circuit of the prior art (FIG. 20) and the circuits disclosed herein is that with the circuits disclosed herein, both a SGS reservoir (18) and a FGS reservoir (20) are in the rigid box. With the valve configurations disclosed herein, there will be sequential delivery of the FGS, then the SGS, when V̇E exceeds the FGSF. This does not occur with the standard anesthetic circle circuit, even if the CO2 absorber is removed from the circuit.

Figure 15:
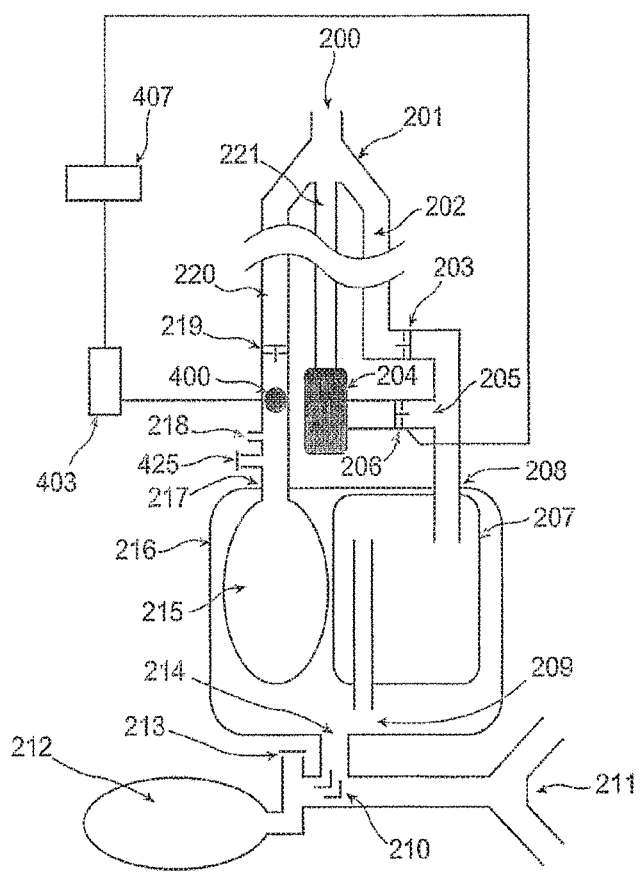
FIG. 15 is a new circuit designed to allow measurement of cardiac output while delivering anesthetics or removing volatile agents from a patient.
Figure 16:
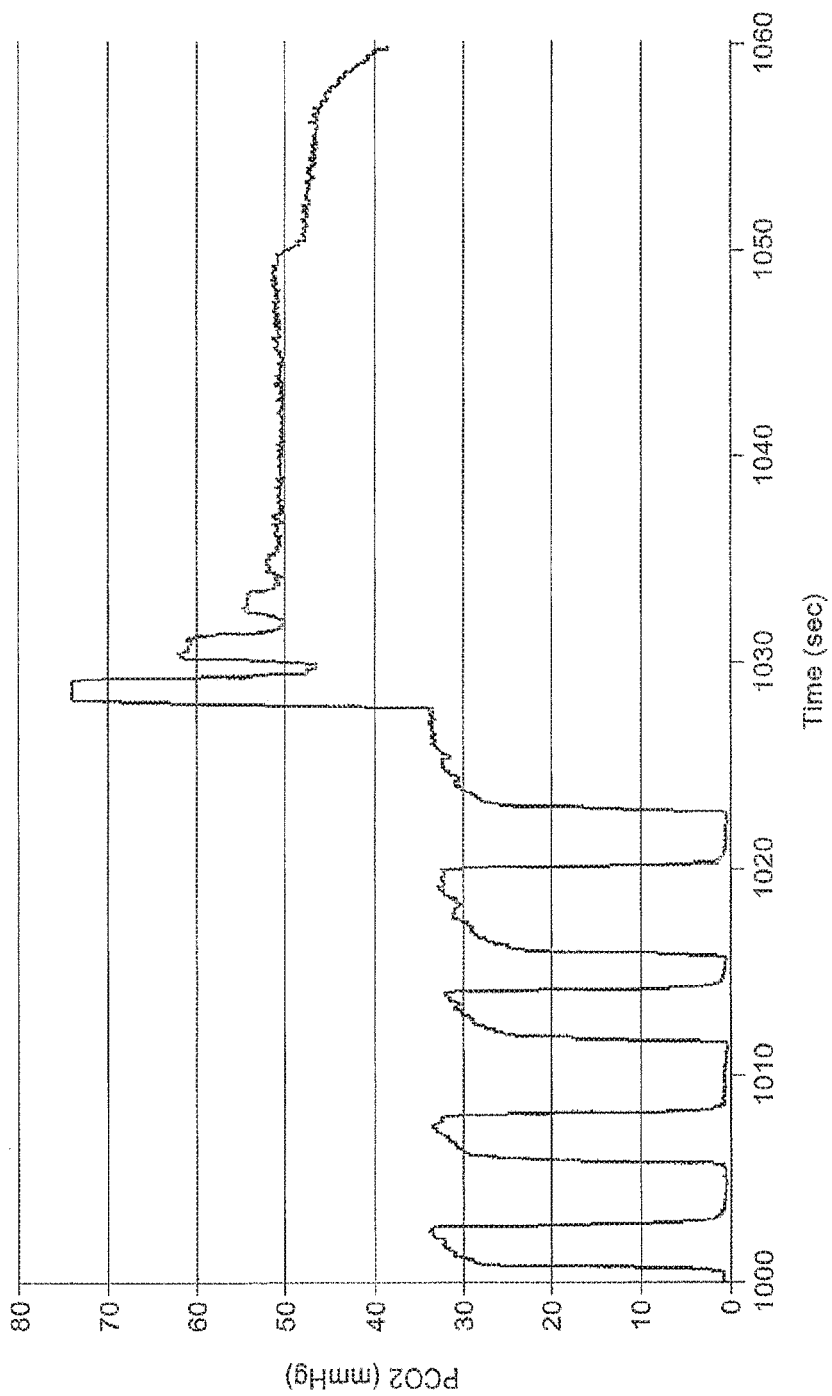
FIG. 16: $PCO_2$ vs. time tracing during a rebreathing equilibrium test for determining oxygenated mixed venous $PCO_2$
Figure 17:
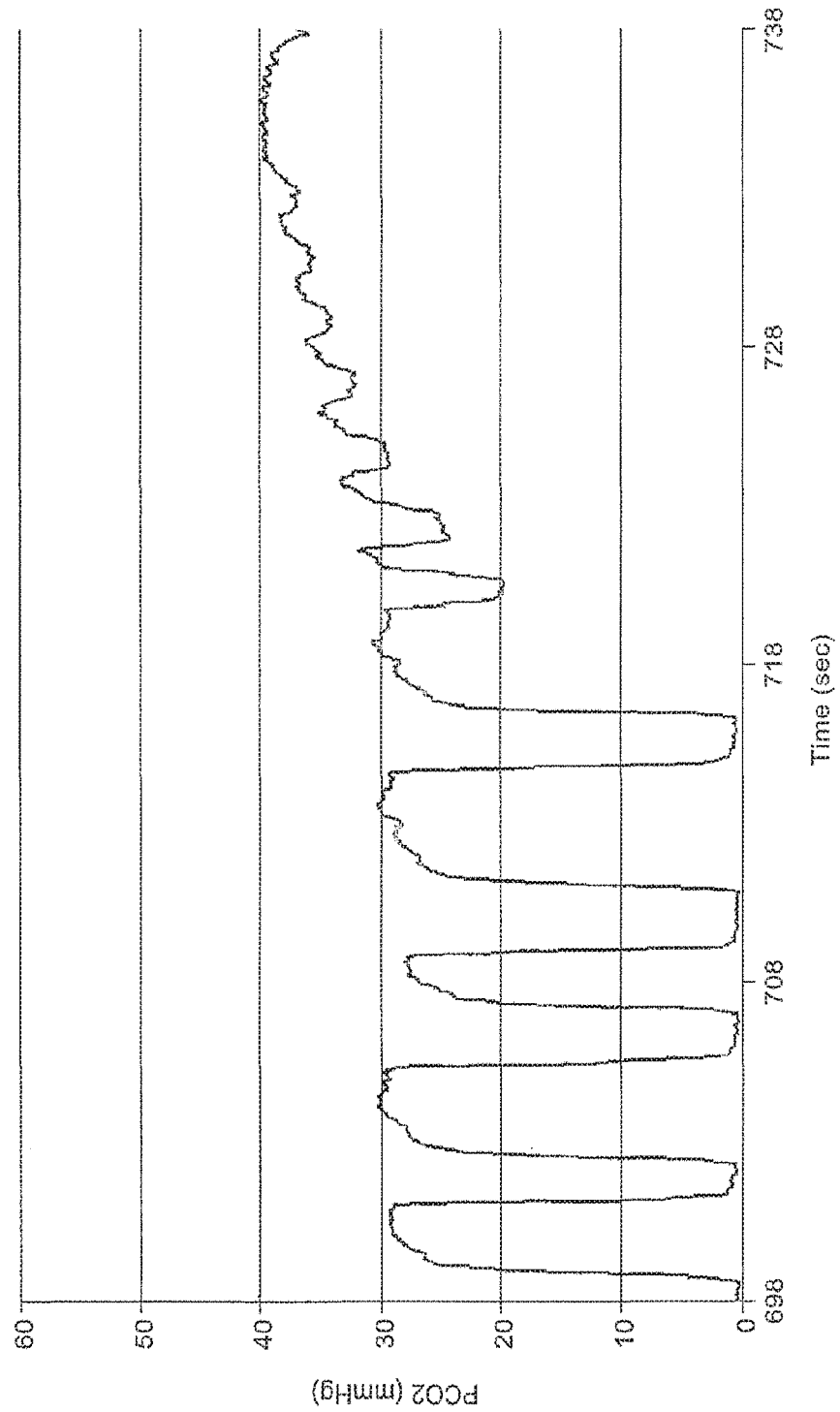
FIG. 17: $PCO_2$ vs. time tracing during exponential method of finding oxygenated mixed venous $PCO_2$

Circuit for Calculation of Q̇ and Related Physiologic Parameters while Modifying Second Gas Set FIG. 15 shows the preferred circuit for measuring cardiac output while maintaining the ability to modify the SGS. The circuit consists of the following components:

| | |
|---|---|
| 200 | patient port |
| 201 | three-port connector |
| 202 | expiratory limb |
| 203 | expiratory valve |
| 204 | canister on bypass conduit that may be switched to be empty, contain $CO_2$ absorbing crystals, zeolyte, charcoal or similar substance that filters anesthetic agents, or hopcalite for filtering carbon monoxide |
| 205 | bypass conduit. |
| 206 | one-way bypass valve with opening pressure slightly greater than that of the inspiratory valve (219) |
| 207 | SGS reservoir bag |
| 208 | port in rigid container for entrance of expiratory limb of circuit in an air- tight manner |
| 209 | exit port for expired gas from expired gas reservoir |
| 210 | a 2-way manual valve that can be turned so that the gas in the rigid box (216) is continuous with either the ventilator Y piece (211) or the manual ventilation assembly consisting of ventilating bag (212) and APL valve (213) |
| 211 | the ventilator Y piece |
| 212 | the ventilation bag |
| 213 | APL valve |
| 214 | ventilation port in rigid box (216) |
| 215 | FGS reservoir |
| 216 | rigid box |
| 217 | port in rigid container for entrance of inspiratory limb of circuit (220) in an air-tight manner |
| 218 | FGS inlet port |
| 219 | inspiratory valve |
| 220 | inspiratory limb |
| 221 | bypass limb proximal to canister (204) |
| 400 | active FGS Control valve |
| 403 | valve control means |
| 407 | bypass valve opening sensing means |

Function of the Circuit as an Anesthetic Circuit:

For spontaneous ventilation, 3-way valve (210) is open between rigid container (216) and manual ventilation assembly consisting of ventilation bag (212) and APL valve (213).

When the patient exhales, increased pressure in the circuit closes inspiratory valve (219) and bypass valve (206). Exhaled gas is directed into the exhalation limb (202), past one-way valve (203) into the expiratory reservoir bag (207). FGS enters via port (218) and fills the FGS reservoir (215). During inhalation, inhalation valve (219) opens and FGS from the FGS reservoir (215) and FGS port (218) enter the inspiratory limb (220) and are delivered to patient. If FGSF is less than $\dot{V}E$, the FGS reservoir (215) empties before the end of the breath; continued respiratory effort results in a further reduction in pressure in the circuit. When the opening pressure of the bypass valve (206) is exceeded, it opens and gas from the expiratory gas reservoir (207) passes through the canister (204) into the rebreathing limb (221) and makes up the balance of the breath with SGS. The opening of bypass valve (206) is detected by valve opening sensing means (407) signals are sent to close FGS control valve (400) by activating valve control means (403). When the FGS control valve (400) is closed, any additional FGSF entering the circuit during the balance of inspiration is directed only to the FGS reservoir bag (215) and not to the patient. When valve (400) is closed patient receives only SGS for the balance of inspiration. FGS control valve (400) may be re-opened any time from the beginning of expiration to just before the next inspiration. Phase of ventilation is sensed by sensor (407).

For the purposes of functioning as an anesthetic delivery circuit, part of the FGS entering the circuit would be the anesthetic vapor, for example Desflurane, and the canister (204) would contain $CO_2$ absorbent material. The SGS passes through the canister (204) but still contains expired $O_2$ and anesthetic, which can both be safely rebreathed by the patient. In this respect, the circuit in FIG. 15 functions like a circle anesthetic circuit in which the FGSF containing $O_2$ and anesthetic can be reduced to match the consumption or absorption by the patient. However, by bypassing the canister (204), the circuit can be used for measuring cardiac output.

If the canister (204) is filled with hopcalite it can be used to remove carbon monoxide from the patient, since the SGS still contains expired $O_2$ and $CO_2$. If the canister (204) is filled with zeolite it can be used to remove volatile agents such as anesthetics from the patient.

Advantages of Circuit Over Previous Art:
1) It is comparable to the circle anesthesia circuit with respect to efficiency of delivery of anesthesia, and ability to conduct anesthesia with spontaneous ventilation as well as controlled ventilation.
2) It is often important to measure tidal volume and VE during anesthesia. With a circle circuit, a pneumotach with attached tubing and cables must be placed at the patient interface, increasing the dead-space, bulk and clutter at the head of the patient. With our circuit, the pneumotach (or a spirometer if the patient is breathing spontaneously) can be placed at port (214) and thus remote from the patient.
3) Sasano (Anesth Analg 2001; 93:1188-1191) taught a circuit that can be used to accelerate the elimination of anesthesia. However that circuit required additional devices such as an external source of gas (reserve gas), a demand regulator, self-inflating bag or other manual ventilating device, 3-way stopcock and additional tubing. Furthermore, Sasano did not disclose a method whereby mechanical ventilation can be used. In fact it appears that it cannot be used—patients must be ventilated by hand for that method. With the apparatus and method disclosed herein, there is no requirement for an additional external source of gas or demand regulator;
4) the patient can be ventilated with the ventilation bag (212) already on the circuit or the circuit ventilator, or any ventilator; no other tubing or devices are required.
5) Circle circuits cannot deliver FGS and then SGS sequentially. Such control is required to make physiological measurements such as cardiac output during anesthesia.

With the circuit of FIG. 15, if the canister (204) is bypassed, the circuit becomes the equivalent of the one described in FIG. 9 with the addition of the ventilator apparatus shown in FIG. 7. With the circuit of FIG. 15, box (216) could be opened to atmosphere instead of connected to a ventilator, and the circuit could be used with spontaneously breathing patients for measuring cardiac output while modifying SGS.

It should be recognized to those skilled in the art that various embodiments of the invention disclosed in this patent application are possible without departing from the scope including, but not limited to:
a) using multiple inspiratory and expiratory limbs in combination provided that:
   i) the inspiratory and expiratory limbs are kept separate except at a single point prior to reaching the patient where they are joined
   ii) each limb has the corresponding valves as in the arrangement above, and
   iii) the valves have the same relative pressures so as to keep the inspired gas delivery sequential as discussed above.
b) using active valves, for example electronic, solenoid, or balloon valves, instead of passive valves, provided said valves are capable of occluding the limbs, and means is provided for triggering and controlling said active valves. The advantage of active valves is more precise control. The disadvantage is that they are more costly.
c) replacing reservoir bags with extended tubes or other means for holding gases
d) surrounding valves in exhalation limb and/or in the inspiratory limb of circuit with the exhaled gas reservoir causing them to be surrounded by warm exhaled air and prevent freezing and sticking of valves in cold environments.
e) Changing the composition of FGS and SGS to change alveolar concentrations of gases other than $CO_2$, for example $O_2$. By analogy to CO2, with respect to $O_2$: alveolar $PO_2$ is determined by FGS flow and the $PO_2$ of FGS. When $PO_2$ of SGS is the same as the $PO_2$ in the alveoli, inhaling SGS does not change flux of $O_2$ in the alveoli. Therefore, those skilled in the art can arrange the partial pressure of component gases in FGS and SGS and the flows of FGS such that they can achieve any alveolar concentration of component gases independent of $\dot{V}E$, as long as $\dot{V}E$ exceeds sufficiently flow of FGS.

As many changes can be made to the various embodiments of the invention without departing from the scope thereof; it is intended that all matter contained herein be interpreted as illustrative of the invention but not in a limiting sense.

To clarify the function of the automated cardiac output device, we will contrast it to a standard anaesthetic machine which has the same configureation of listed components.
1) The preferred SGDB circuits we describe differ from any anaesthetic circuit. The SGDB circuit first provides the FGS, then the SGS. This allows the circuit to compensate for changes in $CO_2$ elimination on any particular breath. For example, during a small breath, the unused FGS remains in the FGS reservoir and is available to provide the exact additional $\dot{V}A$ for each gas in the set when a larger breath is taken or frequency of breathing increases subsequently. As a result, changes in $\dot{V}CO_2$ can be instituted independent of breathing pattern.

2) Anesthetic machines do not automatically alter the fresh gas flows. Fresh gas flows are manually controlled by the anesthesiologist.
3) Anesthetic machines do not calculate $\dot{V}A$ and cannot calculate $\dot{V}CO_2$, and $\dot{Q}$.
4) Anesthetic machines cannot generate the data required to make the calculations for $\dot{Q}$ and its associated parameters because the circuit is inappropriate and the gas flows are not configured to be controlled by a computer.
5) The flowmeters on commonly used anesthetic machines are too imprecise and inaccurate to perform these tests and calculations. There is no need for such precision and accuracy of flow for routine clinical anesthetic care.

Figure 19:
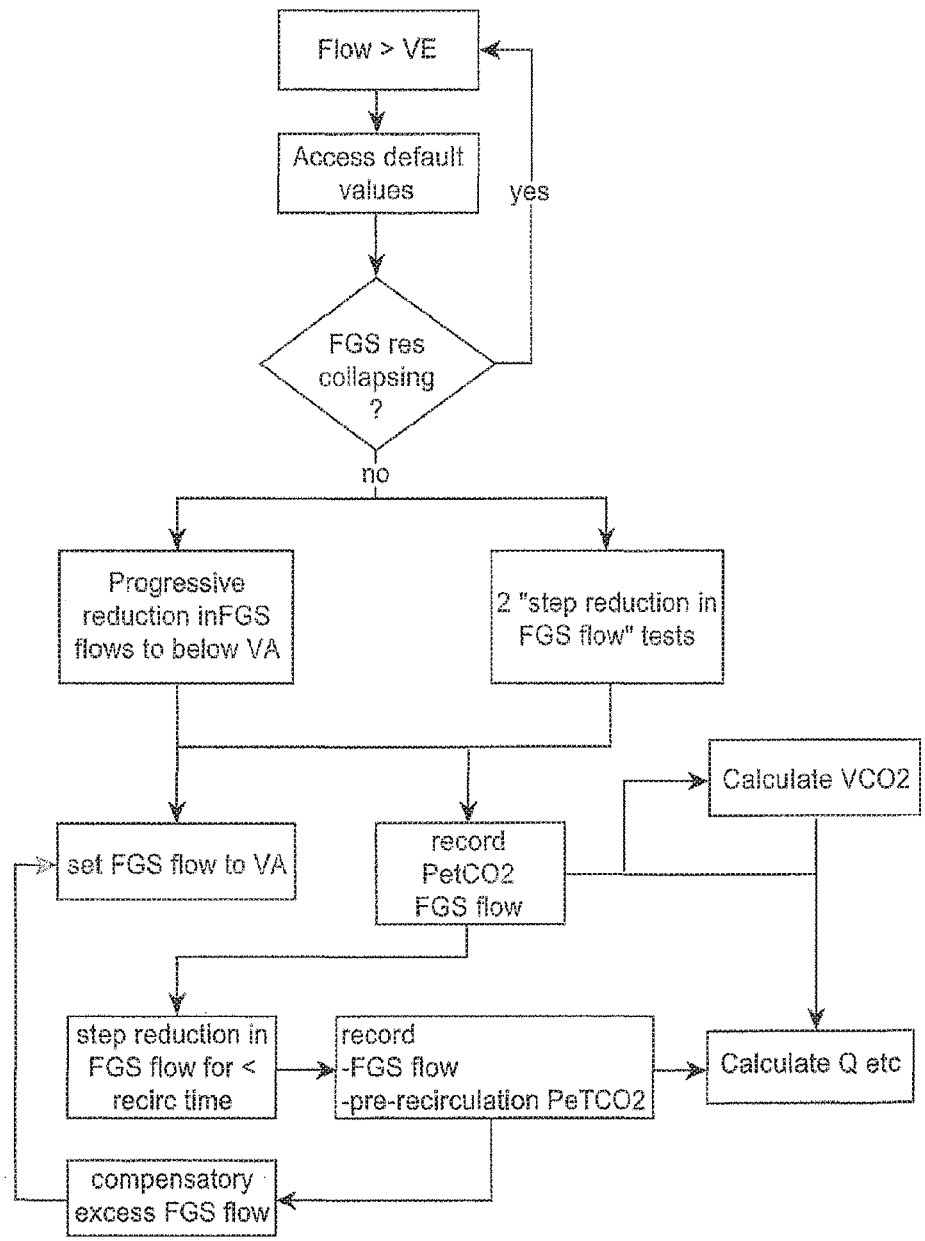
FIG. 19: Flow diagram describing automated sequence of events performed by the non-invasive cardiac output apparatus in order to automatically generate and record data non-invasively and calculate $\dot{Q}$ and other physiologic parameters.
Figure 21:
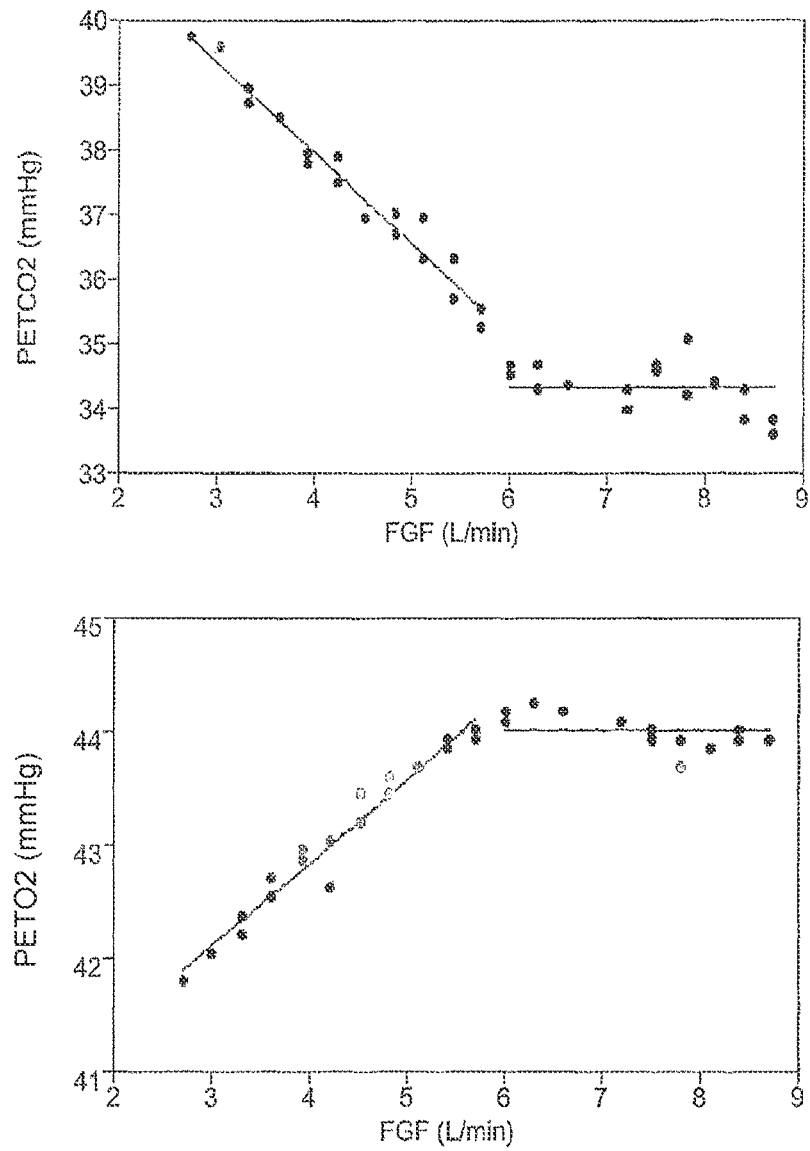
FIG. 21: A detail of the computer screen output of an automated analysis of test finding $\dot{V}_A$ by progressive reduction in SGF flow method in a subject is illustrated in FIG. 21. The figure illustrates that progressive reduction of SGF (labelled "FGF" in the figure) results in a distinct inflection point when either $PETCO_2$ or $PETO_2$ is graphed as a function of SGF.

9.0 Method of generating data required to make calculations of $\dot{Q}$ and related physiologic parameters (see FIG. 19):

Cardiac Output can be measured in several ways according to the methods and apparatus disclosed herein. These include:

9.1 Set-Up Phase
9.1.1 Set Flow of FGS>$\dot{V}E$
9.1.2 Access default values
9.1.3 Check pressure sensor or $PCO_2$ sensor during inhalation. If fresh gas reservoir collapsed or $CO_2$ is detected during inhalation, increase FGS flow until the reservoir until reservoir does not collapse fully and no $CO_2$ is detected during inhalation
9.1.4 Identify $PETCO_2$ from the $CO_2$ gas analyzer
9.2 Find $\dot{V}A$ Via One of Two Methods:
9.2.1 Calculate $\dot{V}A$ by inducing two reductions in FGS flow below $\dot{V}A$ without first identifying $\dot{V}A$ by following the following steps:
9.2.1.1 Calculate a preliminary minimum $\dot{V}A$ for the subject based on body weight, temperature, sex and other parameters known to those skilled in the art.
9.2.1.2 Provide luxuriant FGS flow greater than the patient's resting $\dot{V}E$ until steady state $PETCO_2$, is reached
9.2.1.3 Impose a VA by setting FGS Flow below assumed $\dot{V}A$, to $\dot{V}A^x$ preferably just below the calculated preliminary $\dot{V}A$, for a time less than or equal to a recirculation time, and measure $PETCO_2^x$, the end tidal $CO_2$ concentration during equilibrium if an equilibrium end tidal value is reached within a recirculation time, otherwise it is the equilibrium value of end tidal $CO_2$ as extrapolated from the exponential rise in end tidal $CO_2$ values within the recirculation time.
9.2.1.4 Set FGS flow above $V_E$ until steady state $PETCO_2$ is reached as identified by a less than a threshold change in $PETCO_2$ over a designated time period. The actual thresholds and time periods are user defined according to the circumstances of the test and can be determined by those skilled in the art.
9.2.1.5 Impose a $\dot{V}A$ by setting FGS Flow below assumed $\dot{V}A$, to $\dot{V}A^y$ where $\dot{V}A^y$ is less than calculated preliminary minimum $\dot{V}A$ and not equal to $\dot{V}A^x$, for a time approximately equal to a recirculation time, about 30 s at rest. Measure $PETCO_2^x$, the end tidal $CO_2$ concentration during equilibrium if an equilibrium end tidal value is reached within a recirculation time, otherwise it is the equilibrium value of end tidal $CO_2$ as extrapolated from the exponential rise in end tidal $CO_2$ values within the recirculation time.
9.2.1.6 On a graph of $PETCO_2$ vs FGS flow, plot the points ($PETCO_2^y$, $\dot{V}A^y$) and ($PETCO_2^x$, $\dot{V}A^x$). Extrapolate the line formed by connecting these two point to intersect a horizontal line at $PETCO_2$=resting $PETCO_2$. The FGS flow at the intersection point is determined to be $\dot{V}A$.
9.2.2 Progressive Reduction of FGS flow method of finding $\dot{V}A$:
9.2.2.1 Use FGS that preferably has no $CO_2$
9.2.2.2 Wait for steady state as indicated by less than a threshold change in $PETCO_2$ over a designated time period. The actual thresholds and time periods are user defined according to the circumstances of the test and can be determined by those skilled in the art.
9.2.2.3 When in steady state, reduce FGS flow by a small fixed flow, for example 0.1 L/min, preferably at regular intervals of time or after each breath. Alternate flow reduction rates could be used, and the reduction need not be linear in time.
9.2.2.4 When $PETCO_2$ begins to rise above a threshold value which is approximately the mean steady state $PETCO_2$, continue the reduction in the FGS flow for a time approximately equal to one recirculation time.
9.2.2.5 After approximately one recirculation time, usually about 30 s, raise FGS flow above resting $\dot{V}E$. A relation of $PETCO_2$ vs FGS flow is calculated and two lines of best fit are calculated, one for the set of steady state $PETCO_2$ values, and one for the set of raised $PETCO_2$ values above the mean of the steady state values. The FGS flow corresponding to the intersection of said lines corresponds to $\dot{V}A$. FIG. 21 illustrates that progressive reduction of SGF (labelled "FGF" in the figure) results in a distinct inflection point when either $PETCO_2$ or $PETO_2$ is graphed as a function of SGF. We define the SGF corresponding to this inflection point as equal to $\dot{V}A$.
9.2.2.6 These two methods of finding $\dot{V}A$ are physiologically equivalent and one may have some advantages over the other in particular clinical or research circumstances. The Progressive Reduction method should be contrasted with the method for calculating $\dot{V}A$ taught by Preiss et al. (Canadian Patent Application 2346517). In that method, while fresh gas flow into a sequential gas delivery circuit was reduced stepwise, after each reduction, the subject was observed for several breaths looking for an exponential rise in $PETCO_2$. The Preiss method requires continued breathing at each fresh gas flow looking for development of a new steady when fresh gas flow falls below $\dot{V}A$. This process is very time consuming and is unlikely to be tolerated by most patients. If, in the attempt to shorten the time for finding the fresh gas flow below $\dot{V}A$ the fresh gas flow reduction are large, resolution of critical fresh gas flow is lost. If the steps are small, when the fresh gas flow is just barely less than $\dot{V}A$, it will be difficult to discern the small rise in $PETCO_2$ from the normal variation in $PETCO_2$. The progressive breath-by-breath reduction in FGS flow disclosed herein results in a rapid linear rise in PETCO$_2$ and fall in PETO$_2$, both of which can be used to identify the FGS flow corresponding to $\dot{V}A$ as illustrated in FIG. 21.

9.3 Calculations with the Differential Fick Equation

There are two methods of calculating cardiac output with the Differential Fick equation. (It is understood that the general methods are disclosed without the details well known to those skilled in the art of the multiple standard corrections for temperature, moisture, barometric pressure and the like):

9.3.1 Find $\dot{V}A$ by the Progressive Reduction of FGS flow method of finding $\dot{V}A$:

9.3.1.1 Find $\dot{V}A$ 9.3.1.2 Set FGS Flow=$\dot{V}A$ and calculate $\dot{V}CO_2$ using the equation $\dot{V}CO_2=\dot{V}A\times FETCO_2$.

9.3.1.3 Impose a transient step change in $\dot{V}A$ to $\dot{V}A'$ for a time approximately equal to a recirculation time, about 30 s at rest, by changing FGS flow to a value below $\dot{V}A$. To fully automate the process, select a $\dot{V}A'$ that will be below the $\dot{V}A$. Calculate $\dot{V}CO_2'=\dot{V}A'\times FETCO_2'$. Where $FETCO_2'$ is the fractional end tidal $CO_2$ concentration during equilibrium if an equilibrium end tidal value is reached within a recirculation time, otherwise it is the equilibrium value of end tidal $CO_2$ as extrapolated from the exponential rise in end tidal $CO_2$ values within the recirculation time.

9.3.1.4 Calculate $\dot{Q}$ according to the differential Fick equation using $\dot{V}CO_2$, $\dot{V}CO_2'$, and $CCO_2$ and $CCO_2'$ where $CCO2$ and $CCO_2'$ are the contents of $CO_2$ of end capillary blood as calculated from PETCO$_2$, and PETCO$_2'$ using known relationships between PETCO$_2$, and other characteristics related to the blood such as hemoglobin concentration, temperature oxygen partial pressure and other parameters that are accessible or can be used as default values by those skilled in the art.

9.3.1.5 Calculate $\dot{Q}$ according to the differential Fick equation using $\dot{V}CO_2$ and PETCO$_2$ data from steady state phase and step change phase and the PaCO$_2$ from the Kim Rahn Farhi method. This allows the identification of the PETCO$_2$—PaCO2 gradient without an arterial blood sample.

9.3.2 Generate required data by inducing two reductions in FGS flow below $\dot{V}A$ without first identifying $\dot{V}A$ by following the following steps:

9.3.2.1 Calculate a preliminary minimum $\dot{V}A$ for the subject based on body weight, temperature, sex and other parameters known to those skilled in the art.

9.3.2.2 Provide luxuriant FGS flow greater than the patient's resting $\dot{V}E$ until steady state PETCO$_2$ is reached 9.3.2.3 Impose a $\dot{V}A$ and hence a $\dot{V}CO_2$ by setting FGS Flow below preliminary calculated $\dot{V}A$, to $\dot{V}A^x$ preferably just below the preliminarily calculated $\dot{V}A$, for a time less than or equal to a recirculation time, and calculate $\dot{V}CO_2^x$ using the equation $\dot{V}CO_2^x=\dot{V}A^x\times FETCO_2^x$ where $FETCO_2$ is the fractional end tidal $CO_2$ concentration during equilibrium if an equilibrium end tidal value is reached within a recirculation time, otherwise it is the equilibrium value of end tidal $CO_2$ as extrapolated from the exponential rise in end tidal $CO_2$ values within the recirculation time.

9.3.2.4 Set FGS flow above $V_E$ until steady state PETCO$_2$ is reached as identified by a less than a threshold change in PETCO$_2$ over a designated time period. The actual thresholds and time periods are user defined according to the circumstances of the test and can be determined by those skilled in the art.

9.3.2.5 Impose a transient step change in $\dot{V}A$ to $\dot{V}A^y$ where $\dot{V}A^y$ is less than calculated $\dot{V}A$ and not equal to $\dot{V}A^x$, for a time approximately equal to a recirculation time, about 30 s at rest. Calculate $\dot{V}CO_2^y=\dot{V}A^y\times FETCO_2^y$. $FETCO_2^y$ is the end tidal $CO_2$ concentration during equilibrium if an equilibrium end tidal value is reached within a recirculation time, otherwise it is the equilibrium value of end tidal $CO_2$ as extrapolated from the exponential rise in end tidal $CO_2$ values within the recirculation time.

9.3.2.6 Calculate $\dot{Q}$ according to the differential Fick equation using $\dot{V}CO_2^x$, $\dot{V}CO_2^y$, and and $CCO_2^x$ and $CCO_2^y$ where $CCO_2^c$ and $CCO_2^y$ are the contents of $CO_2$ of end capillary blood as calculated from PETCO$_2^x$, and PETCO$_2^y$ using known relationships between PETCO$_2$, and other characteristics related to the blood such as hemoglobin concentration, temperature oxygen partial pressure and other parameters that are accessible or can be used as default values by those skilled in the art.

9.3.2.7 Calculate $\dot{Q}$ according to the differential Fick equation using $\dot{V}CO_2$ and PETCO$_2$ data from steady state phase and step change phase and the PaCO$_2$ from the Kim Rahn Farhi method to identify the PETCO$_2$—PaCO$_2$ gradient. This allows the identification of the PETCO$_2$—PaCO$_2$ gradient without an arterial blood sample.

Difference between this method and previous methods to perform the differential Fick:

(a) With the new method, the decrease in $\dot{V}CO_2$ is performed by reducing the FGF to a SGDB circuit as opposed to insertion of a deadspace at the patient-circuit interface. As a result, if the subject increases his breathing rate or breath size, there is no change in $\dot{V}CO_2$ and the calculations via the differential Fick equation are not affected.

(b) The $\dot{V}CO_2$ is known using the $\dot{V}A$ (identified by one of the new or the previously disclosed method) and the PETCO$_2$, two robust and highly reliable measures. This is unlike the need for a pneumotachymeter and the error-prone breath-by-breath analysis of $\dot{V}CO_2$ required by previous art.

(c) $\dot{V}A$ is not identified with the previous differential Fick methods.

(d) The PETCO$_2$ to PaCO$_2$ gradient is calculated from two independently derived values in the same subject. In the previous art, this gradient is calculated from empirical formulae derived from averaged values and do not necessarily apply to the subject.

Therefore our method provides more accurate values for $\dot{V}CO_2$, $\dot{V}$, $CO_2'$ and PaCO$_2$ than the previous art.

9.4 Kim-Rahn-Farhi 9.4.1 A period of reduced FGS flow simulates complete or partial breath holding. The PETCO$_2$ of each breath is equivalent to a sequential alveolar sample in the KRF prolonged exhalation method. The substitution of sequential PETCO$_2$ values for sequential samples from a single exhalation is used to calculate true $P\bar{v}CO_2$, $P\bar{v}CO_2$-oxy, PaCO$_2$ and hemoglobin $O_2$ saturation in mixed venous blood $S\bar{v}O_2$ using the Kim Rahn Farhi method.

9.4.2 $\dot{Q}$ can be calculated using the Fick approach where the $P\bar{v}CO_2$-oxy and PaCO$_2$ as calculated by the Kim Rahn Farhi method are used to calculate the respective $CO_2$ contents using methods well known to those skilled in the art, and the $\dot{V}CO_2$ is as calculated from $\dot{V}A$ and $FETCO_2$ as derived in the sequence of steps described above.

9.4.3 Mixed venous $O_2$ hemoglobin saturation are calculated as follows. $\dot{V}O_2$ is calculated from $\dot{V}O_2=\dot{V}A\times(FIO_2-FETO_2)$ where $FIO_2$ and $FETO_2$ are the fractional concentration of inspired and end tidal $O_2$ respectively. Using $\dot{V}O_2$, $\dot{Q}$ as calculated by Differential Fick or Kim Rahn Farhi or Fisher Method, end capillary $O_2$ oxygen content (assuming end capillary blood is fully saturated with oxygen), Mixed venous $O_2$ saturation can be calculated from the standard Fick equation.

9.4.4 Information regarding the arterial $O_2$ hemoglobin saturation ($SaO_2$) (as read from a non-invasive commonly available pulse oximeter that makes the measurement by shining an infrared light through a finger), and the $S\bar{v}O_2$ can be used to calculate the fraction of shunted blood ($\dot{Q}s$) (assuming fully oxygenated blood in the end pulmonary capillary) by using the following equation $$\dot{Q}s = \frac{(SPO_2)\dot{Q}t - (SaO_2)\dot{Q}p}{S\bar{v}O_2}$$

Our method of performing the Kim Rahn Farhi is an improvement over the previous art in that
  (a) Test is performed simultaneously with a test for differential Fick in spontaneously breathing subject.
  (b) Data are pooled with the test as outlined above so calculation of $CO_2$, is simultaneous to the other calculations. In the previous art, the $\dot{V}CO_2$, calculation cannot be done during a breath hold or simulated breath hold by rebreathing.
  (c) $\dot{V}CO_2$, measurement does not require a pneumotachymeter which is expensive, cumbersome and error-prone. In the previous art, $\dot{V}CO_2$, required for the calculation of $\dot{Q}$ required additional apparatus such as pneumatchymeter or gas collection and volume measuring apparatus.

9.5 Fisher E-I Test
9.5.1 Calculate $\dot{V}A$ from the calibration phase, set FGS flow=$\dot{V}A$.
9.5.2 With FGS Flow at $\dot{V}A$, the $PCO_2$ in the FGS is changed to any value and held at that value for a time approximately equal to a recirculation time, about 30 s at rest.
9.5.3 $P\bar{v}CO_2$-oxy is calculated using the $PETCO_2-PICO_2$ method described by Fisher.

Our method of the Fisher E-I test is an improvement over the previous art in that the effect of change in breath size on the equilibrium value of $PETCO_2$ is minimized by the SGDB circuit such that a larger breath delivers physiologically neutral previously expired gas instead of additional test gas.

10.0 Method of Finding $\dot{V}E$ Using Progressive Reduction of FGS Flow:
  10.1 Use FGS that Preferably has No $CO_2$
  10.2 Wait for steady state as indicated by less than a threshold change in $PETCO_2$ over a designated time period. The actual thresholds and time periods are user defined according to the circumstances of the test and can be determined by those skilled in the art.
  10.3 When in steady state, reduce FGS flow by a small fixed flow, for example 0.1 L/min, preferably at regular intervals of time or after each breath. Alternate flow reduction rates could be used, and the reduction need not be linear in time.
  10.4 Using a means for measuring pressure within the FGS reservoir in the breathing circuit, for example a pressure transducer, monitor when the FGS reservoir bag first collapses. $\dot{V}E$ is the FGS flow rate when the reservoir bag first collapses.

11.0 Method for Measuring Anatomical Dead Space
  11.1 Measure $\dot{V}E$ and $\dot{V}A$ using any of the methods disclosed above
  11.2 Measure the respiratory rate, preferably using the apparatus for cardiac output disclosed herein.
  11.3 Calculate Anatomical Dead Space $\dot{V}DAN=(\dot{V}E-\dot{V}A)$/respiratory rate As many changes can be made to the various embodiments of the invention without departing from the scope thereof; it is intended that all matter contained herein be interpreted as illustrative of the invention but not in a limiting sense.

REFERENCE LIST (1) Ganz W, Donoso R, Marcus H S, Forrester J S, Swan H J. A new technique for measurement of cardiac output by thermodilution in man. Am J Cardiol 1971; 27(4):392-396.

(2) Stetz C W, Miller R G, Kelly G E, Raffin T A. Reliability of the thermodilution method in the determination of cardiac output in clinical practice. Am Rev Respir Dis 1982; 126(6):1001-1004.

(3) Critchley L A, Critchley J A. A meta-analysis of studies using bias and precision statistics to compare cardiac output measurement techniques. J Clin Monit Comput 1999; 15(2):85-91.

(4) Imhoff M, Lehner J H, Lohlein D. Noninvasive wholebody electrical bioimpedance cardiac output and invasive thermodilution cardiac output in high-risk surgical patients. Crit Care Med 2000; 28(8):2812-2818.

(5) Koobi T, Kaukinen S, Kauppinen P. Comparison of methods for cardiac output measurement. Crit Care Med 2001; 29(5):1092.

6) Osterlund B, Gedeon A, Krill P, Johansson G, Reiz S. A new method of using gas exchange measurements for the noninvasive determination of cardiac output: clinical experiences in adults following cardiac surgery. Acta Anaesthesiol Scand 1995; 39(6):727-732.

7) Richard R, Lonsdorfer-Wolf E, Charloux A, Doutreleau S, Buchheit M, Oswald-Mammosser M et al. Non-invasive cardiac output evaluation during a maximal progressive exercise test, using a new impedance cardiograph device. Eur J Appl Physiol 2001; 85(3-4):202-207.

(8) Nottin S, Vinet A, Lecoq A M, Guenon P, Obert P. [Study of the reproducibility of cardiac output measurement during exercise in pre-pubertal children by doppler echocardiography and CO2 inhalation]. Arch Mai Coeur Vaiss 2000; 93(11):1297-1303.

(9) Sakka S G, Reinhart K, Wegscheider K, Meier-Hellmann A. Is the placement of a pulmonary artery catheter still justified solely for the measurement of cardiac output? J Cardiothorac Vase Anesth 2000; 14(2):119-124.

(10) Zollner C, Haller M, Weis M, Morstedt K, Lamm P, Kilger E et al. Beat-to-beat measurement of cardiac output by intravascular pulse contour analysis: a prospective criterion standard study in patients after cardiac surgery. J Cardiothorac Vasc Anesth 2000; 14(2):125-129.
(11) Nakonezny P A, Kowalewski R B, Ernst J M, Hawkley L C, Lozano D L, Litvack D A et al. New ambulatory impedance cardiograph validated against the Minnesota Impedance Cardiograph. Psychophysiology 2001; 38(3): 465-473.
(12) Jin X, Weil M H, Tang W, Povoas H, Pernat A, Xie J et al. End-tidal carbon dioxide as a noninvasive indicator of cardiac index during circulatory shock. Crit Care Med 2000; 28(7):2415-2419.
(13) Preiss D A. A new method for measurement of carbon dioxide flux in the lungs during breathing. Toronto: Graduate Department of Chemical Engineering and applied Chemistry, University of Toronto, 2003.

We claim:

1. A method of identifying alveolar ventilation ($V_A$) in a subject, the method comprising:
    (1) using a breathing circuit configured to:
        i. on exhalation by the subject, keep exhaled gas substantially separate from inhalation gas, and
        ii. on inhalation by the subject, when a first gas set (FGS) flow is less than a minute ventilation ($V_E$) of the subject, first provide FGS flow to the subject, and then provide a balance of the $V_E$ of the subject that is substantially a second gas set (SGS);
    (2) setting the FGS flow into the breathing circuit at a rate greater than the $V_E$ of the subject;
    (3) measuring an end tidal $CO_2$ concentration ($PETCO_2$) in a steady state;
    (4) progressively lowering the FGS flow into the circuit, either breath by breath or continuously, until after a time equal to a recirculation time of $CO_2$ within the subject after a rise in $PETCO_2$ values above a threshold value is observed; and
    (5) deriving $V_A$ as the rate of FGS flow at a point of the intersection between two lines comprising:
        (a) an average $PETCO_2$ in steady state; and
        (b) a straight line fit to the $PETCO_2$ values after the rise in $PETCO_2$ values begins until the recirculation time.

\* \* \* \* \*